United States Patent
Kawanishi

(10) Patent No.: US 6,376,168 B1
(45) Date of Patent: Apr. 23, 2002

(54) METHOD FOR PREPARING NON-PHOTOSENSITIVE FATTY ACID SILVER SALT GRAIN

(75) Inventor: Naoyuki Kawanishi, Minami-ashigara (JP)

(73) Assignee: Fuji Photo Film Co., Ltd., Kanagawa (JP)

( * ) Notice: Subject to any disclaimer, the term of this patent is extended or adjusted under 35 U.S.C. 154(b) by 0 days.

(21) Appl. No.: 09/599,722

(22) Filed: Jun. 23, 2000

(30) Foreign Application Priority Data

Jun. 25, 1999 (JP) .......................................... 11-180369

(51) Int. Cl.$^7$ ................................................. G03C 1/00
(52) U.S. Cl. ......................................... 430/620; 554/74
(58) Field of Search ................................ 430/620, 617, 430/619; 554/74

(56) References Cited

U.S. PATENT DOCUMENTS 6,040,130 A * 3/2000 Alton et al. ................. 430/619
6,096,486 A * 8/2000 Emmer et al. ............... 430/350

FOREIGN PATENT DOCUMENTS

| EP | 0 903 627 A1 | 3/1999 |
| EP | 0 903 628 A2 | 3/1999 |
| EP | 0 962 814 A1 | 12/1999 |

OTHER PUBLICATIONS

T. Hayashi, et al., "Effects of Impurities in Pure Silver Behenate Upon the Photographiccharacteristics of Thermally Processed Silver Film" Imaging Abstracts, GB, Royal Photographic Society, London, no. Part 05, 1989, p 276 XP000071381, ISSN: 0896–100 X.

Derwent Abstract of JP–A–8–234358 (1996).

* cited by examiner

Primary Examiner—Thorl Chea
(74) Attorney, Agent, or Firm—Sughrue Mion, PLLC

(57) ABSTRACT

Provided is a method for producing non-photosensitive fatty acid silver salt comprising the steps of reacting a silver ion-containing solution, the solvent of which being a mixture of an organic solvent and water or water, with a solution of an alkali metal salt of a fatty acid, solvent of which being water, organic solvent or a mixture of an organic solvent and water, to obtain a fatty acid silver grain; adding a dispersing agent; and desalting the obtained fatty acid silver dispersion by ultra-filtration; characterized in that pH of the dispersion is kept at 6 or above during a period from a point of time immediately after the addition of the dispersing agent to a point of time an electric conductivity of the filtrate drops below 2000 $\mu$S/cm but not lower than 500 Ats/cm by the desalting operation. The non-photosensitive fatty acid silver salt thus prepared is excellent in fog preventive property, time-dependent fog preventive property, image stability after heat development and light transmissivity, when applied to a heat-developable photosensitive material.

20 Claims, 1 Drawing Sheet

METHOD FOR PREPARING NON-PHOTOSENSITIVE FATTY ACID SILVER SALT GRAIN

TECHNICAL FIELD

The present invention relates to a method for preparing fatty acid silver salt and a heat-developable photosensitive material incorporating the fatty acid silver salt obtained by such preparation method.

RELATED ART

A strong need for reducing the volume of waste process solution has arisen in recent medical field from viewpoints of environmental preservation and space saving. Thus a technology related to a photosensitive heat-developable photographic material for medical diagnosis and photographic purposes has been desired, the material being such that affording efficient light exposure with a laser image setter or laser imager, and providing a black image with high resolution and sharpness. Such photosensitive heat-developable photographic material can provide the user with a more simple and environment-conscious image producing system using no solution-base process chemicals.

The image producing method based on heat development is disclosed, for example, in U.S. Pat. Nos. 3,152,904 and 3,457,075 and "Thermally Processed Silver Systems" written by D. Morgan and B. Shely, Imaging Processes and Materials, Neblette's 8th ed., edited by Sturge, V. Walworth and A. Shepp, p.2, (1989).

Such photosensitive material contains an organic reducible non-photosensitive silver source (e.g., organic acid silver salt), a catalytic amount of photocatalyst (e.g., silver halide) and a reducing agent for silver, all of which being generally dispersed in an organic binder matrix. While the photosensitive material is stable at the room temperature, it will produce silver through a redox reaction between the reducible silver source and the reducing agent when heated to a high temperature (80° C. or above, for example) after light exposure. The redox reaction is promoted by a catalytic action of the latent image produced by the light exposure. That is, the silver generated by the reaction of the reducible silver within the exposed area provides a black spot, which makes a contrast with the non-exposed area and is recognizable as an image.

The silver source employed by such system generally refers to a silver salt of a fatty acid, and a variety of methods for producing thereof have been known. Examples of the methods include such that preparing an organic acid silver salt in a concomitant solution of water and water-insoluble solvent as disclosed for example in JP-A-49-93310 (the code "JP-A" as used herein means an "unexamined published Japanese patent application"), JP-A-49-94619 and JP-A-53-68702; such that preparing an organic acid silver salt in an aqueous solution as disclosed in JP-A-53-31611, JP-A-54-4117 and JP-A-54-46709; such that preparing an organic acid silver salt in an organic solvent as disclosed in JP-A-57-186745, JP-A-47-9432 and U.S. Pat. No. 3,700,458. In principle, the organic acid silver salt is obtained by dissolving a fatty acid into water under heating to a temperature of the melting point thereof or above, adding sodium hydroxide or an alkali metal salt under vigorous stirring, and further adding silver nitrate to convert an alkali soap into a silver soap.

The alkali soap forms micell in the aqueous solution, which appears as a milky liquid. The conversion reaction from such micellar state to silver salt, however, often suffers from a problem in production stability. Thus as a measure for obtaining a homogeneous solution of alkali soap, use of a mixed solution of water and alcohol as a solvent is disclosed in JP-A-55-40607.

Now the alkali soap shows alkalinity as its name suggests, and is prepared under a high pH environment. Adding silver nitrate to an alkali solution, however, not only produces silver oxide as a by-product but also results in an undesirable production of silver nucleus by an action of a trace amount of contaminant which inevitably generates during the production and exhibits a high reducing activity under such high-pH environment. Such by-product is quite disadvantageous in that degrading property of the heat-developable photographic material and in particular in that causing undesirable fog. From this viewpoint, a method for obtaining a homogeneous solution to suppress the generation of the by-product is disclosed in JP-A-55-40607, in which fog still remains unsolved.

In JP-A-9-127643, disclosed is a method for producing silver salt based on simultaneous measuring and addition of an alkali metal salt solution and silver nitrate solution, and is specified as simultaneous addition of aqueous sodium behenate solution and isopropyl alcohol. While the method is successful in at least lowering the high pH during the reaction to the medium range and thereby in suppressing the generation amount of silver oxide, fog still cannot totally be cleared due to a weak reducibility of isopropyl alcohol.

As described above, preparation of fatty acid silver salt needs special accounts such that eliminating as possible reducible substances during the formation of fatty acid silver salt, controlling the grain size and controlling the grain form, where all of them cannot be satisfied at a time by the conventional method.

In the production of a heat-developable photosensitive material using the fatty acid silver salt, a photosensitive layer thereof is often formed by coating a coating liquid containing an organic solvent such as toluene, methyl ethyl ketone or methanol. Using an organic solvent as the solvent, however, is not only disadvantageous in terms of safety in the production processes, adverse effects on human body, and high cost ascribable to the solvent recovery or the like, but is also inappropriate in terms of providing an environment-conscious heat-developable photosensitive material.

Thus a method for forming the photosensitive layer using a water-base coating liquid. For example, JP-A-49-52626 and JP-A-53-116144 disclose cases using gelatin as a binder. In JP-A-50-151138, a case using polyvinyl alcohol as a binder is described.

A case with a combined use of gelatin and polyvinyl alcohol is found in JP-A-60-61747. As another exemplary case, the photosensitive layer using a water-soluble polyvinyl acetal as a binder is described in JP-A-58-28737.

As is clear from the above, using a water-soluble binder allows the photgosensitive layer to be formed with awater-base coating liquid and is beneficial from environmental and economic viewpoints. The water-soluble polymer binder is, however, less compatible with the fatty acid silver salts, which will fail in obtaining a coated film with a surface quality agreeable to the practical use, will result in brownish to yellowish tone of the silver image after the development afar from intrinsically preferable black tone and will result in increased fog. Thus only afforded was a heat-developable photosensitive material whose property being significantly degraded and commercially unsuccessful.

In order to obtain practically agreeable quality of the coated surface using the water-base coating liquid containing a fatty acid silver salt, the fatty acid silver salt must be kept in a finely dispersed state in the water-base solution without agglomeration. Discovery of a method for finely dispersing the fatty acid silver salt is thus desired. One method generally accepted relates to such that producing a hydrophobic grain dispersion of a fatty acid silver salt, separating the grain therefrom by filtration to obtain a solid matter, and re-dispersing the solid matter after being mixed with a dispersing agent as described by D. Kloosterboer in Imaging Processes and Materials, Neblette's 8th ed., edited by Sturge, V. Walworth and A. Shepp, p.279, (1989).

Fine dispersion operation of the fatty acid silver salt can be effected by mechanical dispersion in the presence of a dispersing agent using a known pulverizing means (e.g., high-speed mixer, homogenizer, high-speed impact mill, banbury mixer, homomixer, kneader, ball mill, vibration ball mill, epicyclic ball mill, attritor, sand mill, bead mill, colloid mill, jet mill, roller mill, trommel and high-speed stone mill). These methods, however, produce only a coating liquid including a lot of agglomerated grains and thus causative of degraded surface quality, and, worse than all, tend to indiscriminately cleave the primary grains of the fatty acid silver salt which is originally crystallized as a water-insoluble salt, so that excessive silver nuclei are generated on the crystal cleavage plane of the grains and thereby to increase fog.

On the other hand, JP-B-7-119953 (the code "JP-B" as used herein means an "examined Japanese Patent Publication"), JP-A-8-137044 and JP-A-8-238848 disclose methods such that finely dispersing the fatty acid silver salt by pressure treatment. The methods, however, relate to an organic solvent-base dispersion and stand on a basis different from solving the foregoing problem.

In JP-A-9-127643, disclosed is a method such that obtaining a dispersion of the fatty acid silver salt by simultaneous measuring and addition of an alkali metal salt solution and silver nitrate solution, and then directly desalting the dispersion by dialysis or ultra-filtration. This method is preferable at least in that the primary grain obtained in the crystallization process of the fatty acid silver salt can be incorporated as intact into the photosensitive layer without being crushed. The method, however, still suffers from problems in agglomeration of the grain under a condition of high salt concentration, and in thickening during concentration of the dispersion, which makes the method difficult to be accepted as a measure for obtaining a practical coating liquid.

As described above, a stable method for preparing a coating liquid containing in a solvent a fatty acid silver salt capable of affording an excellent coated surface quality and optical properties such as low haze and low fog has not been undiscovered.

It is therefore an object of the present invention to provide a method for preparing a fatty acid silver salt excellent in decreased fog property when incorporated into a heat-developable photographic material, a time-dependent decreased fog property, image stability after the heat development, and light transmissivity. It is a further object of the present invention to provide a method for preparing a stable dispersion of the fatty acid silver salt, which is capable of improving the coated surface quality, without separating nor re-dispersing such salt as a solid matter.

SUMMARY OF THE INVENTION

The present inventors found after extensive investigations for achieving the above object that, in a method for producing a non-photosensitive fatty acid silver salt grain comprising the steps of reacting a silver ion-containing solution and a solution of alkali metal salt of a fatty acid to prepare a fatty acid silver grain, adding thereto a dispersing agent, and desalting the obtained dispersion of the fatty acid silver salt by ultra-filtration, it is possible to prepare the dispersion of the fatty acid silver salt having an excellent property by controlling the pH and temperature of the dispersion within a predetermined range after the addition of the dispersing agent; and also found that a heat-developable photosensitive material using thus-obtained fatty acid silver salt can exhibit an excellent photographic property, which led us to propose the present invention.

That is, according to a first aspect of the present invention, provided is a method for producing non-photosensitive fatty acid silver salt comprising the steps of reacting a silver ion-containing solution, the solvent of which being a mixture of an organic solvent and water or water, with a solution of an alkali metal salt of a fatty acid, solvent of which being water, organic solvent or a mixture of an organic solvent and water, to obtain a fatty acid silver grain; adding a dispersing agent; and desalting the obtained fatty acid silver dispersion by ultra-filtration; characterized in that pH of the dispersion is kept at 6 or above during a period from a point of time immediately after the addition of the dispersing agent to a point of time an electric conductivity of the filtrate drops below 2000 $\mu$S/cm but not lower than 500 $\mu$S/cm by the desalting operation.

In the present invention, the pH of the dispersion is preferably kept within a range from 6 to 8 during a period from a point of time immediately after the addition of the dispersing agent to a point of time an electric conductivity of the filtrate drops below 2000 $\mu$S/cm but not lower than 500 $\mu$S/cm by the desalting operation.

In the present invention, temperature of the dispersion of the fatty acid silver grain is preferably kept within a range from 1 to 250° C., and more preferably 5 to 20° C., during a period from a point of time immediately after the addition of the dispersing agent to a point of time the desalting operation ends.

In one embodiment of the present invention, the ultra-filtration is continued while adding a poor solvent of the dispersing agent after the electric conductivity of the filtrate drops below 1000 $\mu$S/cm but not lower than 500 $\mu$S/cm by the desalting operation. The poor solvent of the dispersing agent is preferably methanol or ethanol.

In the present invention, the dispersion is preferably concentrated to a dispersoid content of 10 to 70 wt %, and more preferably 20 to 50 wt %, after the electric conductivity of the filtrate drops below 300 $\mu$S/cm but not lower than 20 $\mu$S/cm by the desalting operation.

In the present invention, silver preferably exists in excess of alkali metal by 1 to 20 mol % after the reaction.

In the present invention, the dispersing agent is preferably a nonionic amphiphilic substance.

In the present invention, the dispersing agent is preferably added in an amount of 1 to 30 wt %, and more preferably 3 to 20 wt % of the dispersoid.

In the present invention, concentration of the fatty acid silver grain immediately after the reaction is preferably 1 to 10 wt %.

In the present invention, immediately after the desalting operation is completed, the dispersion is concentrated to a fatty acid silver grain content of 15 to 40 wt %, and more preferably 15 to 25 wt %.

In the present invention, sphere-equivalent diameter of the fatty acid silver grain immediately after the reaction is preferably 0.1 to 0.8 µm.

In the present invention, long edge/short edge ratio of the fatty acid silver grain immediately after the reaction is preferably 1 to 4.

In the present invention, aspect ratio of the fatty acid silver grain immediately after the reaction is preferably 2 to 30.

In the present invention, thickness of the fatty acid silver grain immediately after the reaction is preferably 0.01 to 0.20 µm.

According to a second aspect of the present invention, provided is a heat-developable photosensitive material containing a non-photosensitive fatty acid silver salt, a reducing agent for silver ion, a binder and a photosensitive silver halide grain, characterized in that the non-photosensitive fatty acid silver salt is such that prepared by the method of the present invention.

BRIEF DESCRIPTION OF THE DRAWINGS

The above and other objects and features of the invention are apparent to those skilled in the art from the following referred embodiments thereof when considered in conjunction with the accompanied drawing, in which.

DETAILED DESCRIPTION OF THE INVENTION

Figure 1:
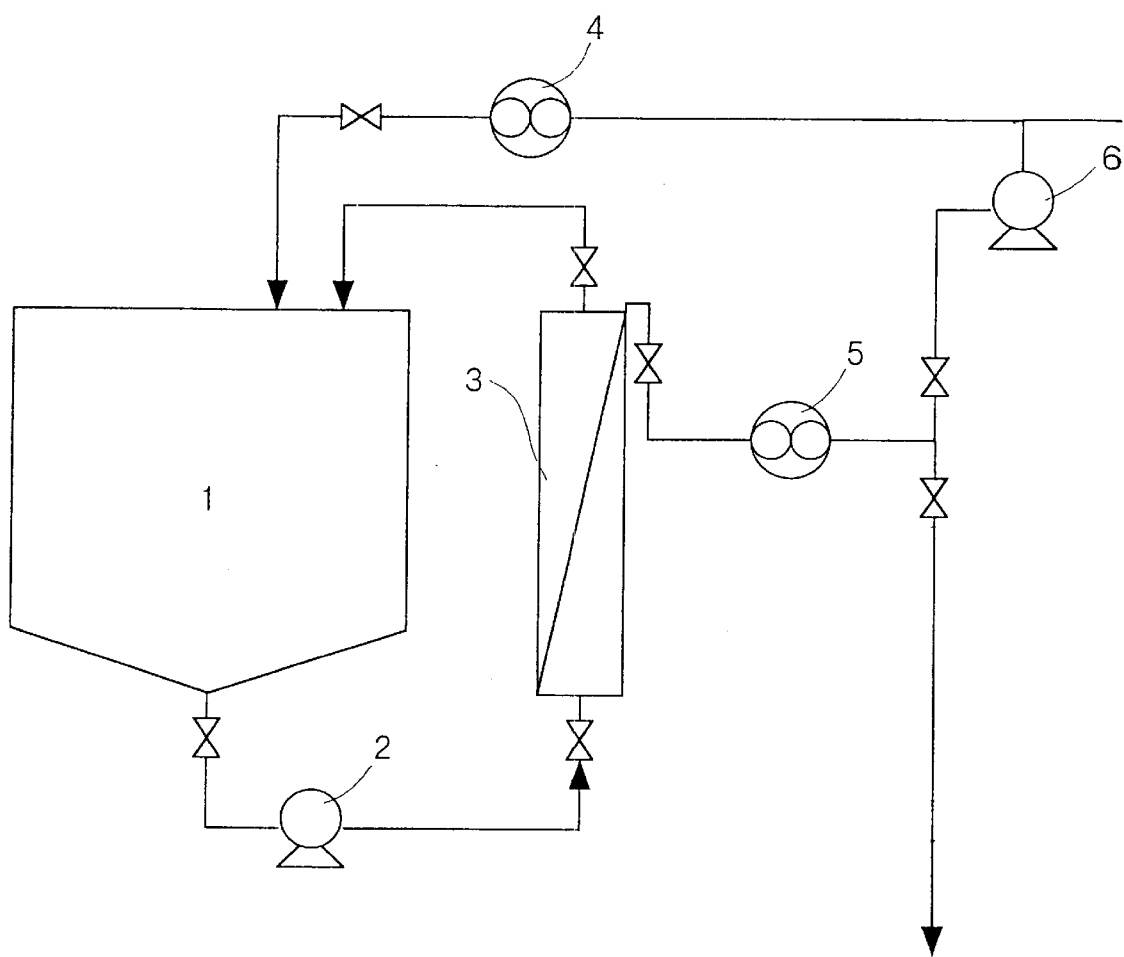
FIG. 1 is a schematic view showing an exemplary constitution of an apparatus used for the ultra-filtration in the present invention, where symbol 1 is used for a tank, 2 for a circulation pump, 3 for a ultra-filtration module, 4 for a flow meter for measuring replenishment water, 5 for a flow meter for measuring permeated water and 6 for a backwash pump.

Modes and methods for carrying out the present invention will be detailed hereinafter.

FIG. 1 shows an exemplary embodiment of a ultra-filtration apparatus used in the present invention. The symbol 1 in the drawing denotes the tank for storing the dispersion of the fatty acid silver salt, from the bottom of which the dispersion is withdrawn with the circulation pump 2 to be fed towards the ultra-filtration module 3 and is then returned to the tank 1 in a closed loop. The circulation pump 2 may be of any type provided that it can afford pressure feeding with a small pulsation width, examples of which include a plunger pump, diaphragm pump, rotary pump and gear pump. The symbol 4 denotes the flow meter for. measuring volume of pure water used for dilution which is effected by replenishing water to the ultra-filtration module causing water loss. This is generally done by volume-constant dilution by which a level control is performed so as to keep the liquid volume within the tank 1 constant. The pure water may contain a pH adjusting agent, a dispersing agent or a poor solvent for the dispersing agent. The symbol 5 denotes the flow meter for measuring permeated water, which is effectively used for detecting clogging of the module or leakage due to the deterioration thereof, and discharges waste liquid in the right lower direction in the drawing. The symbol 6 denotes the pump enabling so-called backwash, by which pure water is fed from the outside of a membrane when foreign matters or the like deposits on the surface of the membrane of the ultra-filtration module and thus the filtration property degrades. In this embodiment, volume of water for the backwash can be quantified with the aid of the flow meter 5.

The method for producing the non-photosensitive fatty acid silver salt grain of the present invention involves addition of a dispersing agent after a fatty acid silver grain is prepared by reacting a silver ion-containing solution with a solution of an alkali metal salt of a fatty acid, and desalting the obtained fatty acid silver dispersion by ultra-filtration. In such preparation method, a fatty acid silver dispersion with an excellent property can be obtained if pH of the dispersion is kept at 6 or above during a period from a point of time immediately after the addition of the dispersing agent to a point of time an electric conductivity of the filtrate drops below 2000 µS/cm but not lower than 500 µS/cm by the desalting operation.

In the present invention, the silver ion is supplied as contained in an aqueous solution or in a mixed solution of water and an organic solvent. On the other hand, the alkali metal salt of the fatty acid is supplied as contained in an aqueous solution, a mixed solution of water and an organic solvent, or in an organic solvent solution.

The silver ion-containing solution used in the present invention preferably has a pH of 1 to 6, and more preferably 1.5 to 4. Any acid or base can be added for further pH adjustment.

Silver ion concentration of the silver ion-containing solution used in the present invention may arbitrarily be selected, where a preferable range as expressed in molar concentration is from 0.03 to 6.5 mol/L, and more preferably 0.1 to 5 mol/L.

To successfully form the fatty acid silver salt grain in the present invention, at least one of the silver ion-containing solution, the alkali metal salt solution of the fatty acid and a solution preliminarily provided in the reaction field must contain an organic solvent in an amount so that the alkali metal salt of the fatty acid can fully be dissolved to give a substantially transparent solution, rather than forming rod-like aggregates or micells. While single use of an organic solvent is also allowable, use of a mixed solution with water is more preferable.

The organic solvent used in the present invention may be of any type so far as having water solubility and above-described properties, whereas those adversely affecting photographic properties are not preferable. Examples of such solvent include water-miscible alcohol and acetone, and more preferable examples relate to tertiary alcohol having a carbon number of 4 to 6.

The fatty acid composing the alkali metal salt of the fatty acid is such that being capable of generating a silver salt which is relatively stable against the light, but can produce silver image when heated at 80° C. or higher in the presence of light-exposed photocatalyst (e.g., latent image of photo-sensitive silver halide) and the reducing agent. The fatty acid is preferably a long-chained fatty carboxylic acid specifically having a carbon number of 10 to 30, more preferably 12 to 26. Preferable examples of the fatty carboxylic acid include cerotic acid, lignoceric acid, behenic acid, erucic acid, arachidinic acid, stearic acid, oleic acid, lauric acid, caproic acid, myristic acid, palmitic acid, maleic acid, fumaric acid, tartaric acid, linolic acid, butyric acid, cam-phoric acid and mixtures thereof.

The alkali metal composing the alkali metal salt of the fatty acid used in the present invention is typified as sodium or potassium. The alkali metal salt of the fatty acid can be obtained by adding NaOH or KOH to the fatty acid, in which it is preferable to limit an amount of use of the alkali metal less than that of the fatty acid so that a part of the fatty acid will remain unreacted. An amount of the residual fatty acid is 3 to 50 mol % relative to the total fatty acid, and preferably 3 to 30 mol %. It is also allowable in the preparation to add an excessive amount of an alkali and then add acid such as nitric acid or sulfuric acid to neutralize the excessive portion of the alkali.

The silver-ion containing aqueous solution or mixed solution with an organic solvent; the aqueous solution or mixed solution with an organic solvent or organic solvent solution of the alkali metal salt of the fatty acid; or a solution preliminarily charged in a reaction vessel to which two above solutions will be charged may be added with a dispersing agent such as, for example, a compound expressed by the general formula (1) of JP-A-62-65035, a water-soluble N-heterocyclic compound having a solubility-expressing group as disclosed in JP-A-62-150240, an inorganic peroxide as disclosed in JP-A-50-101019, a sulfur compound as disclosed in JP-A-51-78319, a disulfide compound as disclosed in JP-A-57-643 and hydrogen peroxide.

The mixed solution of water and the organic solvent dissolving the alkali metal salt of the fatty acid preferably contains the organic solvent in an amount of 3 to 70 vol % of water volume, and preferably 5 to 50 vol %. Since an optimum solvent volume can vary depending on the reaction temperature, it is preferable to determine the optimum volume in a trial-and-error manner.

Concentration of the alkali metal salt of the fatty acid used in the present invention is preferably 5 to 50 wt %, more preferably 7 to 45 wt %, and still more preferably 10 to 40 wt %.

A predetermined fatty acid silver salt can be prepared by simultaneously adding the silver ion-containing aqueous solution or mixed solution with an organic solvent, and the aqueous solution or mixed solution with an organic solvent or organic solvent solution of the alkali metal salt of the fatty acid. In such a case, it is preferable that 10 to 100%, more preferably 30 to 100%, and still more preferably 50 to 100% of the total amount of addition of silver is added simultaneously with the aqueous solution or the mixed solution with the organic solvent containing a nearly equal molarity of the alkali metal salt of the fatty acid. When either solution is precedently added, the silver ion-containing solution in precedence is more preferable.

Temperature of the silver-ion containing aqueous solution or mixed solution with an organic solvent; or the aqueous solution or mixed solution with an organic solvent or organic solvent solution of the alkali metal salt of the fatty acid may appropriately be selected depending on the purpose of the present invention. The temperature of the silver-ion containing solution is preferably selected to 1 to 60° C., and more preferably 5 to 40° C., for the purpose of ensuring stability of the liquid. The temperature of the solution of the fatty acid alkali metal salt is preferably 50 to 90° C., and more preferably 60 to 85° C., for the purpose of keeping a certain temperature required for avoiding crystallization or solidification of the alkali soap.

Temperature of the reaction liquid during the formation of the silver salt may be arbitral and preferably 5 to 70° C., more preferably 10 to 50° C., and still more preferably 20 to 45° C. Keeping such temperature of the reaction liquid further improves the ability of the photographic photosensitive material.

Various approaches are allowable for the preparation of the fatty acid silver salt grain in the present invention. To obtain the grain appropriate for the present invention, it is preferable to lower solubility of the fatty acid salt in the reaction region. The present inventors have found from the investigations that the longer the duration of the addition became, the smaller the grain size became. It was thus concluded that, to obtain a desired grain size, the reaction period must be determined by a trial-and-error manner.

There is no particular limitation on the apparatus used for producing the silver salt. As for stirring device in particular, a variety of available models include those of bulk stirring type using anchor wing or paddle wing; emulsifying dispersion type such as dissolver and homogenizer; and those based on combination of two of these types. The solvent preliminarily charged in the reaction vessel is typically water, where also available is a mixed solution of water and an organic solvent same as that used in the silver ion-containing solution or the solution of fatty acid alkali metal salt.

Addition of the silver ion-containing solution and the solution of the fatty acid alkali metal salt can be effected in various ways such as adding to the liquid surface, adding through a shower head, injecting within a liquid through an eject nozzle opened in the liquid, adding within a separate chamber submerged within the reaction liquid, providing a static mixer in the piping outside of the tank, and providing a separate vessel equipped with a mixer and adding within the vessel.

Also duration of the addition of the silver ion-containing solution and the solution of fatty acid alkali metal salt is arbitrarily selected, and the addition can be effected at a constant rate, or in a accelerated or decelerated mode according to an arbitrary time function.

Sphere-equivalent diameter of the fatty acid silver salt grain prepared in the present invention is preferably 0.1 to 0.8 $\mu$m, and more preferably 0.1 to 0.6 $\mu$m. Long edge/short edge ratio of the grain is preferably 1 to 4, more preferably 1 to 3, and still more preferably 1 to 2. Aspect ratio of the grain [grain size (circle-equivalent diameter) of the major plane/grain thickness] is preferably 2 to 30, and more preferably 2 to 15. Grain thickness is preferably 0.01 to 0.20 $\mu$m, and more preferably 0.01 to 0.15 $\mu$m. The grains satisfying the above requirements preferably account for 30 to 100% of the projected area of the total grains, more preferably 50 to 100%, and still more preferably 70 to 100%.

Particle size distribution of the organic silver salt is preferably of monodisperse as possible. Coefficient of variation of the grain size of the fatty acid silver salt grain is preferably 20% or below, more preferably 18% or below, and still more preferably 15% or below, where the coefficient of variation is defined as a value obtained by dividing a standard deviation of a grain diameter by the grain diameter and then multiplied by 100. An exemplary procedure for the measurement include irradiating laser light to the fatty acid silver salt dispersed in a solution; deriving an autocorrelation function with respect to the time-dependent fluctuation in the scattered light intensity; and thereby obtaining grain size (volume weighted mean diameter), which is known as the dynamic light scattering method.

To the ultra-filtration conducted in the present invention, methods for desalting/concentration of silver halide emulsion can be applied, description of which are found in Research Disclosure No. 10208 (1972), No. 13122 (1975) and No. 16351 (1977). Pressure difference and flow rate, which are critical operation parameters, can be determined referring to a characteristics curve shown in "Maku Riyo Gijyutsu Handobukku (Handbook of Membrane Utilization Technology)" by Haruhiko Ohya, published by Saiwai Shobo Shuppan (1978), p.275, while it is necessary to find out an optimum condition for suppressing grain agglomeration or fog depending on a target fatty acid silver dispersion to be processed. Replenishment of a solvent lost during the membrane permeation can be conducted by the constant-volume method based on continuous feeding of the solvent, or the batch method based on intermittent portion-wise addition, where the former method being preferred as judged from a relatively short process time for the desalting. Pure water obtained after ion exchange or distillation will successfully be used as a solvent to be replenished, which can also contain a pH adjusting agent, a dispersing agent or a poor solvent for the dispersing agent in order to attain a desirable value for pH, concentration of the dispersing agent or concentration of the poor solvent for the dispersing agent. It is also allowable to add these additives directly to the fatty acid silver dispersion.

The poor solvent for the dispersing agent is exemplified by lower alcohols (e.g., methanol and ethanol).

There are various types of the ultra-filtration membrane such as disc type, spiral type, cylindrical type and hollow fiber type, which are commercially available from Asahi Chemical, Dicel Chemical Industries, Ltd., Toray Industries, Inc. and Nitto Denko Corporation. Among these, the spiral type and hollow fiber type are preferable from the viewpoints of total membrane area and washability. Fractional molecular weight of the membrane, which provides an index for a threshold value of membrane-permeable components, must be determined based on the molecular weight of the dispersing agent being used, which is preferably 5,000 to 50,000, and more preferably 5,000 to 15,000.

A water-soluble dispersing agent can be added to the silver ion-containing solution, solution of fatty acid alkali metal salt or reaction liquid in the present invention. That is, the dispersing agent can be contained in a liquid preliminarily charged in the reaction vessel before the fatty acid silver salt is formed; the reaction liquid in the process of forming the fatty acid silver salt or separately prepared solution of the dispersing agent; or in the finished liquid after the fatty acid silver salt is formed. While the dispersing agent can be of any type so far as it can disperse the generated fatty acid silver salt, preferred is a nonionic amphiphilic substance less sensitive to an electrolyte concentration during the desalting operation by ultra-filtration. Specific examples of the dispersing agent comply with those described later in connection to the fatty acid silver salt.

The fatty acid silver salt free from the dispersing agent has a strong hydrophobicity, so that inter-grain crosslinking will proceed with time, and a shearing field or a pressure field appears in the liquid feeding operation or during the permeation through a ultra-filter membrane will accelerate severe agglomeration of the grains. Such agglomeration will further be promoted in an environment with a high ionic strength before the desalting operation since surface electric charge of the fatty acid silver grains will be shielded. To relieve such situation, it is preferable to raise the pH so as to promote the dissociation of the species present on the surface of the grains. Too strong alkali environment, however, result in increased fog since activity of silver oxide or impurity reducing agent will be enhanced. The present invention is the first to enable a stable ultra-filtration even under a high ionic strength by keeping the pH of the dispersion at 6 or above, and more preferably 6 to 8, until an electric conductivity of the filtrate drops 2000 $\mu$S/cm or below but not lower than 500 $\mu$S/cm by the desalting operation.

The fatty acid silver salt prepared in the present invention must have a scaly shape. It clearly differs from generally-known behenate grains such that, for example, having an needle-like form with a short and long axes as shown in FIG. 2.2 on page 45 of "Handbook of Imaging Materials" edited by A. S. Diamond, published by Marcel Dekker 1991), or having no selective growth direction as disclosed in JP-A-9-127643.

Liquid temperature must be kept low following the addition of the dispersing agent and until the desalting operation progresses. This is because crystal shape will be likely to alter if the dispersing agent is added when an organic solvent used for dissolving an alkali metal salt of a fatty acid remains as immersed in the grains of the produced fatty acid silver. The alteration generally proceeds from a metastable scaly form to an needle-like form. Thus in the present invention, the ultra-filtration operation is preferably performed after the addition of the dispersing agent while keeping the temperature of the fatty acid silver dispersion at 1 to 25° C., and more preferably 5 to 20° C.

According to one embodiment of the present invention, after the electric conductivity of the dispersion drops below 1000 $\mu$S/cm but not lower than 500 $\mu$S/cm as the desalting progresses, the ultra-filtration may be performed while adding a poor solvent for the dispersing agent being used. The fatty acid silver grains will not agglomerate even if the protective action of the dispersing agent is weakened, since a stabilizing tendency due to electric charge on the surface of the grains will appear in an environment of low ionic strength. On the contrary, this may even result in raised viscosity of the entire dispersion due to increased inter-grain repulsion, which will make the filtration operation difficult. The addition of the poor solvent for the dispersing agent is preferable to avoid such problem.

The dispersant can be properly selected from, for example, synthetic anionic polymers such as polyacrylic acid, copolymers of acrylic acid, maleic acid copolymers, maleic acid monoester copolymers and acryloylmethylpropanesulfonic acid copolymers; semisynthetic anionic polymers such as carboxymethylated starch and carboxymethylcellulose; anionic polymers such as alginic acid and pectic acid; anionic surfactants such as disclosed in JP-A-52-92716 and WO88/04794; compounds disclosed in JP-A-9-179243; known anionic, nonionic and cationic surfactants; other known polymers such as polyvinyl alcohol, polyvinylpyrrolidone, carboxymethyl cellulose, hydroxypropyl cellulose, and hydroxypropylmethyl cellulose; naturally occurring polymers such as gelatin and the like.

A concentration of the dispersing agent is preferably 1 to 30 wt % of the fatty acid silver salt, and more preferably 3 to 20 wt %.

The produced dispersion can be stored under stirring in order to prevent precipitation of the micrograins during storage, or stored in a highly viscous state by producing hydrophilic colloid (e.g., jelly state formed with gelatin). Further, it may be added with a preservative in order to prevent germ proliferation during the storage.

The fatty acid silver salt dispersion obtained by the present invention comprises at least a fatty acid silver salt and water. While there is no specific limitation on the ratio of the fatty acid silver salt and water, it is important to select the ratio so as to ensure an efficient film formation, considering rheological characteristics required for the stable coating, and the production speed depending on the dry moisture content. The fatty acid silver salt preferably accounts for 10 to 70 wt % of the total dispersion, and more preferably 20 to 50 wt %.

It is preferable to add a metal ion selected from the group consisting of Ca, Mg, Ce, Al, Zn and Ba in a form of a water-soluble salt, not in a form of a halide. More specifically, the addition in a form of a nitrate or sulfate is preferable.

The metal ion selected from the group consisting of Ca, Mg, Ce, Al, Zn and Ba can be added at any time provided that it is immediately before the coating. That is, it may be added to the solution used for preparing the fatty acid silver salt or may preliminarily added in the reaction liquid; may be added during or immediately after the production of the fatty acid silver salt; or may be added before or after the preparation of the coating liquid. An amount addition of the metal is preferably $10^{-3}$ to $10^{-1}$ mol per mol of the fatty acid silver salt, and more preferably $5 \times 10^{-3}$ to $5 \times 10^{-2}$ mol.

The non-photosensitive fatty acid silver salt obtained by the present invention can be used for a heat-developable photosensitive material together with a photosensitive silver halide. Such heat-developable photosensitive material is hereinafter referred as the heat-developable photosensitive material of the present invention.

There is no specific limitation on the composition of the photosensitive silver halide available for the heat-developable photosensitive material of the present invention, and examples of which include silver chloride, silver chlorobromide, silver bromide, silver iodobromide and silver iodochlorobromide. Halogen composition distribution within the grain may be uniform, or may change stepwise or continuously. Silver halide grain with a core/shell structure may also preferably be used, in which the structure thereof is preferably of double-shelled to quintuple-shelled, and more preferably of double-shelled to quadruple-shelled. It is also preferable to adopt a technique for localizing silver bromide on the surface of silver chloride or silver chlorobromide.

Methods for preparing photosensitive silver halide are well known in the art, and, for example, the methods described in Research Disclosure, No. 17029 (June, 1978) and U.S. Pat. No. 3,700,458 may be applied. More specifically, photosensitive silver halide is prepared by adding a silver source compound and a halogen source compound in a solution containing gelatin or other polymer, which is followed by addition of an organic acid silver salt. The photosensitive silver halide grain preferably has a small grain size so as to avoid haze after image production. Specifically, the grain size is preferably 0.20 μm or less, more preferably from 0.01 to 0.15 μm, still more preferably from 0.02 to 0.12 μm. The term "grain size" as used herein means the length of the edge of the silver halide grain for the case that the grain is of a normal crystal having cubic or octahedral shape; means the diameter of a circle having the same area with the projected area of the major plane of the silver halide grain for the case that the grain has a tabular shape; and means the diameter of a sphere having a volume equal to that of the silver halide grain for the case that the grain is of an irregular crystal having a spherical or rod shape.

Examples of the shape of the silver halide grain include cubic, octahedral, tabular, spherical, rod and pebble; among these, cubic and tabular being in particular preferred in the present invention. When a tabular silver halide grain is used, the average aspect ratio is preferably from 100:1 to 2:1, more preferably from 50:1 to 3:1. A silver halide grain having rounded corners is also preferably used. The plane indices (Miller indices) of the outer surface plane of the photosensitive silver halide grain is not particularly limited; however, it is preferred that [100] plane showing a high spectral sensitization efficiency upon adsorption of the spectral sensitizing dye occuping a large percentage. The percentage is preferably 50% or above, more preferably 65% or above, still more preferably 80% or above. The percentage of a plane with a Miller index of [100] can be determined by the method described in T. Tani, J. Imaging Sci., 29, 165 (1985), which is based on the plane dependency of adsorption of the sensitizing dye between [111] and [100] planes.

The photosensitive silver halide grain for use in the present invention contains a Group VII metal or Group VIII metal in the Periodic Table, or metal complex. The Group VII metal or Group VIII metal in the Periodic Table, or a center metal of the metal complex is preferably rhodium, rhenium, ruthenium, osmium or iridium. These metal complexes may be used individually, or in combination of two or more complexes of the same metal or different metals. The metal complex content is preferably from $1 \times 10^{-9}$ to $1 \times 10^{-3}$ mol per mol of silver, and more preferably from $1 \times 10^{-8}$ to $1 \times 10^{-4}$ mol. With respect to the specific structure of the metal complexes, those having the structures described in JP-A-7-225449 may be used.

As the rhodium compound preferably used in the present invention relates to a water-soluble rhodium compound. Examples thereof include a rhodium(III) halide compounds; and rhodium complex salts having a halogen, amines or an oxalates as ligands, such as hexachlororhodium(III) complex salt, pentachloroaquorhodium(III) complex salt, tetrachlorodiaquorhodium(III) complex salt, hexabromorhodium(III) complex salt, hexaamminerhodium (III) complex salt and trioxalatorhodium(III) complex salt.

These rhodium compounds are used in a dissolved form in water or other appropriate solvent, where a method commonly used for stabilizing the rhodium compound solution may be applied, in which an aqueous hydrogen halide solution (e.g., hydrochloric acid, bromic acid, fluoric acid) or alkali halide (e.g., KCl, NaCl, KBr, NaBr) is added. In place of using the water-soluble rhodium, separate silver halide grains predoped with rhodium may be added and dissolved at the time of preparation of silver halide.

The amount of the rhodium compound added is preferably from $1 \times 10^{-8}$ to $5 \times 10^{-6}$ mol per mol of silver halide, and more preferably from $5 \times 10^{-8}$ to $1 \times 10^{-6}$ mol. The rhodium compound may appropriately be added at the time of production of silver halide emulsion grains or at respective stages before coating of the emulsion, where more preferable is to add the compound at the time of emulsion production to be incorporated into the silver halide grain.

Rhenium, ruthenium or osmium for use in the present invention is added in the form of water-soluble complex salt described in JP-A-63-2042, JP-A-1-285941, JP-A-2-20852 and JP-A-2-20855. An exceptionally preferred example thereof refers to a hexacoordinative complex salt represented by the following formula:

wherein M represents Ru, Re or Os; and n represents 0, 1, 2, 3 or 4. In this case, ammonium or alkali metal ion is used as counter ion, while the counter ion being of no importance. Preferred examples of the ligand include halide ligand, cyanide ligand, cyanoxide ligand, nitrosyl ligand and thionitrosyl ligand. Specific examples of the complex for use in the present invention are shown below, while not being limited thereto.

| | | |
|---|---|---|
| $[ReCl_6]^{3-}$ | $[ReBr_6]^{3-}$ | $[ReCl_5(NO)]^{2-}$ |
| $[Re(NS)Br_5]^{2-}$ | $[Re(NO)(CN)_5]^{2-}$ | $[Re(O)_2(CN)_4]^{3-}$ |
| $[RuCl_6]^{3-}$ | $[RuCl_4(H_2O)_2]^{-}$ | $[RuCl_5(H_2O)]^{2-}$ |
| $[RuCl_5(NO)]^{2-}$ | $[RuBr_5(NS)]^{2-}$ | $[Ru(CO)_3Cl_3]^{2-}$ |
| $[Ru(CO)Cl_5]^{2-}$ | $[Ru(CO)Br_5]^{2-}$ | $[OsCl_6]^{3-}$ |
| $[OsCl_5(NO)]^{2-}$ | $[Os(NO)(CN)_5]^{2-}$ | $[Os(NS)Br_5]^{2-}$ |
| $[Os(O)_2(CN)_4]^{4-}$ | | |

The amount of addition of these compounds is preferably from $1\times10^{-9}$ to $1\times10^{-5}$ mol per mol of silver halide, and more preferably from $1\times10^{-8}$ to $1\times10^{-6}$ mol. These compounds may be added appropriately at the time of preparation of silver halide emulsion grains or at respective stages before coating of the emulsion, where more preferable is to add the compound at the time of emulsion production to be incorporated into the silver halide grain. As for adding the compound during the grain formation of silver halide and integrating it into a silver halide grain, applicable methods include such that previously adding an aqueous solution of metal complex powder together with or without NaCl or KCl to a solution of water-soluble salt or water-soluble halide during the grain formation; such that adding the compound as the third solution at the time of simultaneously mixing a silver salt and a halide solution to prepare silver halide grains by the triple jet method; and such that pouring a necessary amount of an aqueous metal complex solution into a reaction vessel during the grain formation. Among these, preferred is a method comprising adding an aqueous solution of metal complex powder together with or without NaCl or KCl to a water-soluble halide solution. In order to add the compound to the grain surface, a necessary amount of an aqueous metal complex solution may be charged into a reaction vessel immediately after the grain formation, during or after completion of the physical ripening, or at the time of chemical ripening.

As the iridium compound for use in the present invention, various compounds may be used, and examples thereof include hexachloroiridium, hexammineiridium, trioxalatoiridium, hexacyanoiridium and pentachloronitrosyliridium. These iridium compounds are used in a dissolved form in water or other appropriate solvent, where a method commonly used for stabilizing the iridium compound solution may be applied, in which an aqueous hydrogen halide solution (e.g., hydrochloric acid, bromic acid, fluoric acid) or alkali halide (e.g., KCl, NaCl, KBr, NaBr) is added. In place of using the water-soluble iridium, separate silver halide grains predoped with iridium may be added and dissolved at the time of preparation of silver halide.

The silver halide grain for use in the present invention may further contain a metal atom such as cobalt, iron, nickel, chromium, palladium, platinum, gold, thallium, copper and lead. As for cobalt, iron, chromium and ruthenium compound, hexacyano metal complex is preferably used. Specific examples thereof include ferricyanate ion, ferrocyanate ion, hexacyanocobaltate ion, hexacyanochromate ion and hexacyanoruthenate ion, while not being limited thereto. The phase of the silver halide, in which the metal complex is contained, is not particularly limited, and the phase may be uniform or the metal complex may be contained in a higher concentration in the core portion or in the shell portion. The above-described metal is used preferably in an amount of from $1\times10^{-9}$ to $1\times10^{-4}$ mol per mol of silver halide. The metal may be added at the time of preparation of the grains through converting it into a metal salt in the form of simple salt, double salt or complex salt.

The photosensitive silver halide grain may be desalted by water washing according to a method known in the art, such as noodle washing and flocculation, while omission of the desalting being also allowable in the present invention.

For the case that the silver halide emulsion used in the present invention is subjected to gold sensitization, it is allowable to use gold compounds commonly used in the art, where oxidation number of which maybe 1 or 3. Typical examples of the gold sensitizers include chloroauric acid, potassium chloroaurate, auric trichloride, potassium auric thiocyanate, potassium iodoaurate, tetracyanoauric acid, ammonium aurothiocyanate, and pyridyltrichloro gold.

An amount of addition of the gold sensitizer varies depending on various conditions, where it is generally $1\times10^{-7}$ to $1\times10^{-3}$ mol per mol of silver halide, and more preferably $1\times10^{-6}$ to $5\times10^{-4}$ mol.

It is preferable to combine the gold sensitization for treating the silver halide emulsion used in the present invention with other chemical sensitization. Other chemical sensitization may be of any known method such as sulfur sensitization, selenium sensitization, tellurium sensitization or noble metal sensitization. As for the case that the gold sensitization is combined with other sensitization, preferable combinations include sulfur and gold sensitizations; selenium and gold sensitizations; sulfur, selenium and gold sensitizations; sulfur, tellurium and gold sensitizations; and sulfur, selenium, tellurium and gold sensitizations.

The sulfur sensitization applied to the present invention is usually performed by adding a sulfur sensitizer and stirring the emulsion at a temperature as high as 40° C. or above for a predetermined time. The sulfur sensitizer may be a known compound and examples thereof include, in addition to the sulfur compound contained in gelatin, various sulfur compounds such as thiosulfates, thioureas, thiazoles and rhodanines, among which thiosulfate and thiourea being preferable. Although the amount of the sulfur sensitizer to be added varies depending upon various conditions such as pH, temperature and grain size of silver halide at the time of chemical ripening, it is preferably from $1\times10^{-7}$ to $1\times10^{-2}$ mol per mol of silver halide, and more preferably from $1\times10^{-5}$ to $1\times10^{-3}$ mol.

The selenium sensitizer for use in the present invention may be a known selenium compound. The selenium sensitization is usually performed by adding a labile and/or non-labile selenium compound and stirring the emulsion at a temperature as high as 40° C. or above for a predetermined time. Examples of the labile selenium compound include those described in JP-B-44-15748, JP-B-43-13489, JP-A-4-25832, JP-A-4-109240, JP-A-3-121798 and JP-A-4-324855. Among these, particularly preferred are those expressed by formulae (VIII) and (IX) of JP-A-4-324855.

The tellurium sensitizer for use in the present invention is a compound capable of producing silver telluride, presumably serve as a sensitization nucleus, on the surface or inside of silver halide grain. The rate of the formation of silver telluride in a silver halide emulsion can be examined according to a method described in JP-A-5-313284. Examples of the tellurium sensitizer include diacyl tellurides, bis (oxycarbonyl) tellurides, bis(carbamoyl) tellurides, diacyl ditellurides, bis (oxycarbonyl) ditellurides, bis (carbamoyl) ditellurides, compounds having a P=Te bond, tellurocarboxylates, Te-organyltellurocarboxylic esters, di (poly) tellurides, tellurides, tellurols, telluroacetals, tellurosulfonates, compounds having a P-Te bond, Te-containing heterocycles, tellurocarbonyl compounds, inorganic tellurium compounds and colloidal tellurium. Specific examples thereof include the compounds described in U.S. Pat. Nos. 1,623,499, 3,320,069 and 3,772,031; British Patents No. 235,211, No. 1,121,496, No. 1,295,462 and No.

1,396,696; Canadian Patent No. 800,958; JP-A-4-204640, JP-A-3-53693, JP-A-3-131598, JP-A-4-129787; J. Chem. Soc. Chem. Commun., 635 (1980), ibid., 1102 (1979); ibid., 645 (1979); J. Chem. Soc. Perkin. Trans., 1, 2191 (1980); S. Patai (compiler), The Chemistry of Organic Selenium and Tellurium Compounds, Vol. 1 (1986); and ibid., Vol. 2 (1987). The compounds expressed by formulae (II), (III) and (IV) of JP-A-5-313284 are particularly preferred.

An amount of the selenium or tellurium sensitizer used in the present invention varies depending on silver halide grains used or chemical ripening conditions. However, it is generally from $1 \times 10^{-8}$ to $1 \times 10^{-2}$ mol per mol of silver halide, preferably on the order of from $1 \times 10^{-7}$ to $1 \times 10^{-3}$ mol. The conditions for chemical sensitization in the present invention are not particularly restricted. However, in general, pH is from 5 to 8; pAg is from 6 to 11, preferably from 7 to 10; and temperature is from 40 to 95° C., preferably from 45 to 85° C.

As for the silver halide emulsion for use in the present invention, production or physical ripening process for the silver halide grain may be performed under the presence of cadmium salt, sulfite, lead salt or thallium salt.

In the present invention, reductive sensitization may be adoptable. Specific examples of the compound used in the reductive sensitization include ascorbic acid, thiourea dioxide, stannous chloride, aminoiminomethanesulfinic acid, hydrazine derivative, borane compound, silane compound and polyamine compound. The reductive sensitization may be performed by ripening the grains while keeping the emulsion at pH 7 or above, or at pAg 8.3 or below. Also, the reductive sensitization may be performed by introducing a single addition portion of silver ion during the formation of the grains.

To the silver halide emulsion for use in the present invention, thiosulfonic acid compound may be added by the method described in European Patent No. 293,917A.

In the recording material used for the present invention, a single kind of silver halide emulsion may be used, or two or more kinds of silver halide emulsions (for example, those differ in the average grain size, halogen composition, crystal habit or chemical sensitization conditions) may be used in combination.

An amount of the photosensitive silver halide used in the present invention is preferably from 0.01 to 0.5 mol per mol of the organic acid silver salt, more preferably from 0.02 to 0.3 mol, still more preferably from 0.03 to 0.25 mol.

A preferable timing for adding the silver halide to the coating liquid for image producing layer resides in a period from 180 minutes before to immediately before the coating, and more preferably from 60 minutes before to 10 seconds before. There is no specific limitation on method or conditions for the mixing provided that sufficient effects of the present invention will be obtained. Specific examples of the method include such that using a tank devised so that an average retention time estimated based on the addition flow rate and feed volume to a coater is adjusted to a desired value; and such that using a static mixer described in Chapter 8 of "Ekitai Kongo Gijutsu (Liquid Mixing Technology)" by N. Harnby, M. F. Edwards, and A. W. Nienow, translated by Koji Takahashi, published by Nikkan Kogyo Shinbun-sha (1989).

The heat-developable photosensitive material of the present invention contains a reducing agent for reducing the fatty acid silver salt. The reducing agent for reducing the fatty acid silver salt may be an arbitrary substance capable of reducing silver ion into metal silver, and is preferably an organic substance. While conventional photographic developers such as phenidone, hydroquinone and catechol are also useful, hindered phenol compound is preferable. The reducing agent is preferably contained in an amount of 5 to 50 mol %, and more preferably 10 to 40 mol %, relative to one mol of silver present in elsewhere on the side having the image producing layer. A layer to which the reducing agent is added may be any layer on the side having the image-forming layer. In the case of adding the reducing agent to a layer other than the image forming layer, the reducing agent is preferably used in some larger amount of 10 to 50 mol % per mol of silver. The reducing agent may also be a so-called precursor which is devised to effectively exhibit its function only at the time of development.

As for the heat-developable photosensitive material using the fatty acid silver salt, a wide variety of the reducing agents are disclosed, for example, in JP-A-46-6074, JP-A-47-1238, JP-A-47-33621, JP-A-49-46427, JP-A-49-115540, JP-A-50-14334, JP-A-50-36110, JP-A-50-147711, JP-A-51-32632, JP-A-51-1023721, JP-A-51-32324, JP-A-51-51933, JP-A-52-84727, JP-A-55-108654, JP-A-56-146133, JP-A-57-82828, JP-A-57-82829, JP-A-6-3793, U.S. Pat. Nos. 3,667,9586, 3,679,426, 3,751,252, 3,751,255, 3,761,270, 3,782,949, 3,839,048, 3,928,686 and 5,464,738, German Patent No. 2,321,328 and European Patent No. 692,732.

Examples thereof include amidoximes such as phenylamidoxime, 2-thienylamidoxime and p-phenoxyphenylamidoxime; azines such as 4-hydroxy-3,5-dimethoxybenzaldehyde azine; combinations of an fatty carboxylic acid arylhydrazide with an ascorbic acid, such as a combination of 2,2'-bis(hydroxymethyl)propionyl-β-phenylhydrazine with ascorbic acid; combinations of polyhydroxybenzene with hydroxylamine, reductone and/or hydrazine (e.g., combination of hydroquinone with bis (ethoxyethyl) hydroxylamine, piperidinohexose reductone or formyl-4-methylphenylhydrazine); hydroxamic acids such as phenylhydroxamic acid, p-hydroxyphenylhydroxamic acid and β-anilinehydroxamic acid; combinations of azine and sulfonaimdophenol (e.g., combination of phenothiazine and 2,6-dichloro-4-benzenesulfonamidophenol); α-cyanophenylacetic acid derivatives such as ethyl-α-cyano-2-methylphenyl acetate and ethyl-α-cyanophenyl acetate; bis-β-naphthols such as 2,2'-dihydroxy-1,1'-binaphthyl, 6,6'-dibromo-2,2'-dihydroxy-1,1'-binaphthyl and bis(2-hydroxy-1-naphthyl) methane; combinations of bis-β-naphthol with 1,3-dihydroxybenzene derivative (e.g., 2,4-dihydroxybenzophenone or 2',4'-dihydroxyacetophenone); 5-pyrazolones such as 3-methyl-1-phenyl-5-pyrazolone; reductones such as dimethylaminohexose reductone, anhydrodihydroaminohexose reductone and anhydrodihydropiperidonehexose reductone; sulfonamidophenol reducing agents such as 2,6-dichloro-4-benzenesulfonamidophenol and p-benzenesulfonamidophenol; 2-phenylindane-1,3-dione or the like; chromans such as 2,2-dimethyl-7-t-butyl-6-hydroxychroman; 1,4-dihydropyridines such as 2,6-dimethoxy-3,5-dicarboethoxy-1,4-dihydropyridine; bisphenols such as bis(2-hydroxy-3-t-butyl-5-methylphenyl)methane, 2,2-bis(4-hydroxy-3-methylphenyl) propane, 4,4-ethylidene-bis(2-t-butyl-6-methylphenol), 1,1-bis(2-hydroxy-3,5-dimethylphenyl)-3,5,5-trimethylhexane and 2,2-bis(3,5-dimethyl-4-hydroxyphenyl)propane; ascorbic acid derivatives such as 1-ascorbyl palmitate and ascorbyl stearate; aldehydes and ketones having benzyl and biacetyl groups; 3-pyrazolidone and a certain kind of indane-1,3-diones; and chromanols (e.g., tocopherol). More preferable reducing agent are bisphenol and chromanols.

The reducing agent used in the present invention may be added in any form of solution, powder or solid micrograin dispersion. Dispersion of the solid micrograin is effected using a known pulverizing means (e.g., ball mill, vibrating ball mill, sand mill, colloid mill, jet mill and roller mill). A dispersing agent may be available for dispersing the solid micrograin.

Using an additive known as a color toner may sometimes raise the optical density and preferable in the present invention. In some cases the color toner is even advantageous in forming a blackened silver image. The color toner is preferably contained in elsewhere on the side having the image forming layer in an amount of 0.1 to 50 mol % per mol of silver, and more preferably 0.5 to 20 mol %. The color toner may also be a so-called precursor which is devised to effectively exhibit its function only at the time of development.

As for the heat-developable photosensitive material using the fatty acid silver salt, a wide variety of the color toners are disclosed, for example, in JP-A-46-6077, JP-A-47-10282, JP-A-49-5019, JP-A-49-5020, JP-A-49-91215, JP-A-50-2524, JP-A-50-32927, JP-A-50-67132, JP-A-50-67641, JP-A-50-114217, JP-A-51-3223, JP-A-51-27923, JP-A-52-14788, JP-A-52-99813, JP-A-53-1020, JP-A-53-76020, JP-A-54-156524, JP-A-54-156525, JP-A-61-183642, JP-A-4-56848, JP-B-49-10727, JP-B-54-20333, U.S. Pat. Nos. 3,080,254, 3,446,648, 3,782,941, 4,123,282 and 4,510,236, British Patent No. 1,380,795 and Belgian Patent No. 841,910.

Examples of the color toner include phthalimide and N-hydroxyphthalimide; cyclic imides such as succinimide, pyrazoline-5-one, 1-phenyl urazole, quinazolinone, 3-phenylpyrazoline-5-one, 1-phenylurazole, quinazoline and 2,4-thiazolinedione; naphthalimide (e.g., N-hydroxy-1,8-naphthalimide); cobalt complex (e.g., cobalthexamine trifluoroacetate); mercaptans such as 3-mercapto-1,2,4-triazole, 2,4-dimercaptopyrimidine, 3-mercapto-4,5-diphenyl-1,2,4-triazole and 2,5-dimercapto-1,3,4-thiadiazole; N-(aminomethyl)aryldicarboxyimide (e.g., N,N-(dimethylaminomethyl)phthalimide and N,N-(dimethylaminomethyl)naphthalene-2,3-dicarboxyimide); blocked pyrazole, isothiuronium derivatives, a certain kind of photofading agent [e.g., N,N'-hexa-methylenebis(1-carbamoyl-3,5-dimethylpyrazole, 1,8-(3,6-diazaoctane)bis (isothiuronium trifluoroacetate) and 2-tribromomethylsulfonyl)benzothiazole]; 3-ethyl-5-[(3-ethyl-2-benzothiazolinilidene)-1-methylethylidene]-2-thio-2,4-oxazolidinedione; phthalazinone, phthalazinone derivatives or metal salts; or the derivatives such as 4-(1-naphthyl) phthalazinone, 6-chlorophthalazinone, 5,7-dimethoxyphthalazinone or 2,3-dihydro-1,4-phthalazinedione; combinations of phthalazinone and phthalic acid derivatives (e.g., phthalic acid, 4-methyltphthalic acid, 4-nitrophthalic acid and tetrachlorophthalic anhydride); phthalazines, phthalazine derivatives or metal salts; combinations of phthalazine and phthalic acid derivatives (e.g., phthalic acid, 4-methyltphthalic acid, 4-nitrophthalic acid and tetrachlorophthalic anhydride); quinazolinedione, benzoxazine or natphthoxazine derivatives; rhodium complex serves, not only as a color toner, but also as an in situ halide ion source for producing silver halide, such as ammonium hexachlororhodate (III), rhodium bromide, rhodium nitrate and potassium hexachlororhodate (III); inorganic peroxides and persulfates such as ammonium disulfide peroxide and hydrogen peroxide; benzoxazines such as 1,3-benzoxazine-2,4-dione, 8-methyl-1,3-benzoxazine-2,4-dione and 6-nitro-1,3-benzoxazine-2,4-dione; pyrimidines and asymmetric triazine (e.g., 2,4-dihydroxypyrimidine and 2-hydroxy-4-aminopyrimidine); azauracil; and tetraazapentalene derivatives (e.g., 3,6-dimercapto-1,4-diphenyl-1H,4H-2,3a,5,6a-tetraazapentalene and 1,4-di(o-chlorophenyl)-3,6-dimercapto-1H,4H-2,3a,5,6a-tetraazapentalene).

The color toner may be added in any form of solution, powder or solid micrograin dispersion. Dispersion of the solid micrograin is effected using a known pulverizing means (e.g., ball mill, vibrating ball mill, sand mill, colloid mill, jet mill and roller mill). A dispersing agent may be available for dispersing the solid micrograin.

Effect of the present invention will be enhanced when the organic acid silver salt-containing layer is formed by coating and then drying a coated liquid in which water accounts for 30 wt % or above of the solvent thereof, and in particular when a binder of the organic acid silver salt-containing layer (referred as "polymer in the present invention" hereinafter) comprises a polymer latex which is soluble or dispersible in a water-base solvent (aqueous solvent) and in particular has an equilibrium moisture content at 25° C., 60%RH of 2 wt % or less. Most preferable mode relates to that the polymer latex has an ion conductivity of 2.5 mS/cm or below. Such polymer latex can be obtained by purifying a synthesized polymer using a separation functional membrane.

A water-base solvent capable of solubilizing or dispersing the polymer latex refers to water or water mixed with 70 wt % or less thereof of a water-miscible organic solvent. Examples of the water-miscible solvent include alcohols such as methanol, ethanol and propanol; Cellosolves such as Methyl Cellosolve, Ethyl Cellosolve and Butyl Cellosolve; ethyl acetate and dimethylformamide.

The term "water-base solvent" is also used herein to express a system in which polymer is not solubilized in a thermodynamic sense but is present in a dispersed form.

"The equilibrium moisture content at 25° C., 60%RH" can be expressed by an equation such as equilibrium moisture content at 25° C., $60\%RH = [(W1-W0)/W0] \times 100$ (wt %) where, W1 represents polymer weight under humidity conditioning equilibrium in an environment of 25° C. and 60%RH, and W0 represents polymer weight under bone dry equilibrium.

Definition and measurement method of moisture content can be referred to the description of "Kobunshi Zairyo Shiken-ho (Test Methods for Polymer Materials)" in the series of "Kobunshi Kogaku Koza 14 (Polymer Engineering Course 14)", edited by Polymer Society, published by Chijin Shokan.

An equilibrium moisture content at 25° C., 60%RH of the polymer used in the present invention is preferably 2 wt % or less, more preferably 0.01 to 1.5 wt %, and still more preferably 0.02 to 1 wt %.

The polymer used in the present invention is not particularly limited provided that it is soluble or dispersible in the aforementioned water-base solvent and has an equilibrium moisture content at 25° C., 60%RH of 2 wt % or less. Among such polymers, particularly preferable is that dispersible in the water-base solvent.

Possible dispersion forms include such that micrograins of solid polymer are dispersed to form a latex, and such that polymer molecules are dispersed in a molecular state or form micells, either of which being preferable.

In the present invention, preferably used are hydrophobic polymers such as acrylic resin, polyester resin, rubber-base resin (for example, SBR resin), polyurethane resin, vinyl chloride resin, vinyl acetate resin, vinylidene chloride resin and polyolefin resin. The polymer may be a straight-chained polymer, a branched polymer or a cross-linked polymer. The polymer may be a so-called homopolymer consisting of a single kind of monomer or may be a copolymer consisting of two or more kinds of monomers. Both of random copolymer and block copolymer are allowable as the copolymer. The polymer preferably has a number average molecular weight of from 5,000 to 1,000,000, and more preferably from 10,000 to 200,000. Too small molecular weight will result in poor mechanical strength of the coated film after drying, whereas too large in undesirable film-forming property.

The polymer in the present invention refers to these polymers dispersed in the water-base solvent. The "water-base solvent" refers to a dispersion medium such that 30 wt % or more of the composition of which being composed of water. Any style of dispersion, such as emulsified dispersion, micellar dispersion, and molecular dispersion of polymer having in the molecule a hydrophilic portion, is allowable, and most preferable form is latex.

Preferable examples of the polymer latex are listed below, in which polymers are expressed with source monomers, and numerals in the parentheses denote contents in wt % and the molecular weights represent number average molecular weights:

P-1; latex expressed as -MMA(70)-EA(27)-MAA(3)-(M.W. 37,000),

P-2; latex expressed as -MMA(70)-2EHA(20)-St(5)-AA(5)-(M.W. 40,000),

P-3; latex expressed as -St(50)-Bu(47)-MAA(3)-(M.W. 45,000),

P-4; latex expressed as -St(68)-Bu(29)-AA(3)-(M.W. 60,000),

P-5; latex expressed as -St(70)-Bu(27)-IA(3)-(M.W. 120,000),

P-6; latex expressed as -St(75)-Bu(24)-AA(1)-(M.W. 108,000),

P-7; latex expressed as -St(60)-Bu(35)-DVB(3)-MAA(2)-(M.W. 150,000),

P-8; latex expressed as -St(70)-Bu(25)-DVB(2)-AA(3)-(M.W. 280,000),

P-9; latex expressed as -VC(50)-MMA(20)-EA(20)-AN(5)-AA(5)-(M.W. 80,000),

P-10; latex expressed as -VDC(85)-MMA(5)-EA(5)-MAA(5)-(M.W. 67,000),

P-11; latex expressed as -Et(90)-MAA(10)-(M.W. 12,000),

The abbreviations in the above structures correspond with monomers as follows: MMA=methyl methacrylate, EA=ethyl acrylate, MAA=methacrylic acid, 2EHA=2-ethylhexyl acrylate, St=styrene, Bu=butadiene, AA=acrylic acid, DVB=divinylbenzene, VC=vinyl chloride, AN=acrylonitrile, VDC=vinylidene chloride, Et=ethylene, and IA=itaconic acid.

Such polymers are also commercially available, which include acrylic resins such as CEBIAN A-4635, 46583 and 4601 (all produced by Dicel Chemical Industries, Ltd.) and Nipol Lx811, 814, 821, 820 and 857 (all produced by Nippon Zeon K.K.); polyester resins such as FINETEX ES650, 611, 675 and 850 (all produced by Dai-Nippon Ink & Chemicals, Inc.), WD-size and WMS (both produced by Eastman Chemical); polyurethane resins such as HYDRAN AP10, 20, 30 and 40 (all produced by Dai-Nippon Ink & Chemicals, Inc.); rubber-based resins such as LACSTAR 7310K, 3307B, 4700H and 7132C (all produced by Dai-Nippon Ink & Chemicals, Inc.), Nipol Lx416, 410, 438C and 2507 (all produced by Nippon Zeon K.K.); vinyl chloride resins such as G351 and G576 (both produced by Nippon Zeon K.K.); vinylidene chloride resins such as L502 and L513 (both produced by Asahi Chemical Industry Co., Ltd.); and olefin resins such as CHEMIPEARL S120 and SA100 (both produced by Mitsui Chemical Co., Ltd.).

These polymers may be used individually as a polymer latex or, as required, as a blend of two or more thereof.

A latex of styrene-butadiene copolymer is in particular preferable as the polymer latex used in the present invention. Weight ratio of styrene monomer unit and butadiene monomer unit in the styrene-butadiene copolymer is preferably 40:60 to 95:5. The styrene monomer unit and butadiene monomer unit in together preferably account for 60 to 99 wt % of the copolymer. A preferable range for the molecular weight thereof is the same as described previously.

Examples of the styrene-butadiene copolymer latex preferably used in the present invention include above-described P-3 to P-8, and commercially available LACSTAR-3307B, 7132C and Nipol Lx416.

The fatty acid silver salt-containing layer of the heat-developable photosensitive material of the present invention can optionally be added with hydrophilic polymer such as gelatin, polyvinyl alcohol, methyl cellulose, and hydroxypropyl cellulose. An amount of addition of these hydrophilic polymers is preferably 30 wt % or less of the total binder, and preferably 20 wt % or less.

The fatty acid silver salt-containing layer is formed using the polymer latex, in which a content of the binder in the fatty acid silver salt-containing layer, expressed by a weight ratio of the total binder and the organic silver salt, is preferably 1/10 to 10/1, and more preferably 1/5 to 4/1.

Such fatty acid silver salt-containing layer is also, in general, a photosensitive layer (emulsion layer) containing a photosensitive silver halide as a photosensitive silver salt, and the weight ratio of the total binder and the silver halide is preferably 400 to 5, and more preferably 200 to 10.

An amount of the total binder of the image producing layer is preferably 0.2 to 30 $g/m^2$, and more preferably 1 to 15 $g/m^2$. The image producing layer in the present invention may be added with a cross-linking agent for crosslinking or a surfactant for improving coating property.

In the present invention, the solvent (herein for simplicity, the solvent and dispersoid are inclusively termed as "solvent") is preferably a water-base solvent containing 30 wt % or more thereof of water. Possible component of the coating liquid other than water may be an arbitrary water-miscible organic solvent such as methanol, ethanol, isopropanol, Methyl Cellosolve, Ethyl Cellosolve, dimethylformamide or ethyl acetate. Water content of the solvent for the coating liquid is preferably 50 wt % or above, and more preferably 70 wt % or above. Preferable examples of the solvent composition include water, water/methanol=90/10, water/methanol =70/30, water/methanol/dimethylformamide=80/15/5, water/methanol/Ethyl Cellosolve=85/10/5 and water/methanol/isopropanol=85/10/5 (the numerals are in wt %).

The heat-developable photosensitive material of the present invention may contain a sensitizing dye. The sensitizing dye used in the present invention may arbitrarily be selected from those capable of spectrally sensitizing the silver halide particles at a desired wavelength region by adhering thereon. As such sensitizing dyes, usable are, for example, cyanine dyes, merocyanine dyes, complex cyanine dyes, complex merocyanine dyes, holopolar cyanine dyes, styryl dyes, hemicyanine dyes, oxonole dyes and hemioxonole dyes. Sensitizing dyes which are usable in the present invention are described, for example, in Research Disclosure, Item 17643, IV-A (December, 1978, page 23), ibid. Item 1831X (August, 1978, page 437) and also in the references as cited therein. In particular, sensitizing dyes having a spectral sensitivity suitable for spectral characteristics of light sources of various laser imagers, scanners, image setters, process cameras and the like can advantageously be selected.

Exemplary dyes advantageous for the spectral sensitization to red light from so-called red light sources such as He-Ne laser, red semiconductor laser and red LED, include Compounds I-1 to I-38 disclosed in JP-A-54-18726; Compounds I-1 to I-35 disclosed in JP-A-6-75322; Compounds I-1 to I-34 disclosed in JP-A-7-287338; Dyes 1 to 20 disclosed in JP-B-55-39818; Compounds I-1 to I-37 disclosed in JP-A-62-284343; and Compounds I-1 to I-34 disclosed in JP-A-7-287338.

Spectral sensitization as to the wavelength region of from 750 to 1,400 nm from semiconductor laser light sources can advantageously be obtained with various known dyes such as cyanine dye, merocyanine dye, styryl dye, hemicyanine dye, oxonol dye, hemioxonol dye and xanthene dye. Useful cyanine dyes are those having a basic nucleus such as thiazoline nucleus, oxazoline nucleus, pyrroline nucleus, pyridine nucleus, oxazole nucleus, thiazole nucleus, selenazole nucleus or imidazole nucleus. Useful merocyanine dyes are those having the above-described basic nucleus or an acidic nucleus such as thiohydantoin nucleus, rhodanine nucleus, oxazolidinedione nucleus, thiazolinedione nucleus, barbituric acid nucleus, thiazolinone nucleus, malononitrile nucleus or pyrazolone nucleus. Of these cyanine and merocyanine dyes, those having an imino group or a carboxyl group are particularly effective. The dye may be appropriately selected from known dyes described, for example, in U.S. Pat Nos. 3,761,279, 3,719,495 and 3,877,943, British Patents No. 1,466,201, No. 1,469,117 and No. 1,422,057, JP-B-3-10391, JP-B-6-52387, JP-A-5-341432, JP-A-6-194781 and JP-A-6-301141.

The dyes preferably used in particular for the present invention include cyanine dyes having a thioether bond (e.g., those described in JP-A-62-58239, JP-A-3-138638, JP-A-3-138642, JP-A-4-255840, JP-A-5-72659, JP-A-5-72661, JP-A-6-222491, JP-A-2-230506, JP-A-6-258757, JP-A-6-317868, JP-A-6-324425, JP-W-A-7-500926 (the code "JP-W-A" as used herein means an "international application published in Japanese for Japanese national phase"), and U.S. Pat. No. 5,541,054); dyes having a carboxylic acid group (e.g., dyes disclosed in JP-A-3-163440, JP-A-6-301141, and U.S. Pat. No. 5,441,899); merocyanine dyes; polynuclear merocyanine dyes; and polynuclear cyanine dyes (those disclosed in JP-A-47-6329, JP-A-49-105524, JP-A-51-127719, JP-A-52-80829, JP-A-54-61517, JP-A-59-214846, JP-A-60-6750, JP-A-63-159841, JP-A-6-35109, JP-A-6-59381, JP-A-7-146537, JP-W-A-55-50111, British Patent No. 1,467,638, and U.S. Pat. No. 5,281,515) and the like.

Dyes forming J-band have been disclosed in U.S. Pat. Nos. 5,510,236 and 3,871,887 (Example 5), JP-A-2-96131 andJP-A-59-48753, and the like, and they can preferably be used for the present invention.

These sensitizing dyes may be used either individually or in combination of two or more thereof. The combination of sensitizing dyes is often used for the purpose of supersensitization. In combination with the sensitizing dye, a dye which itself has no spectral sensitization effect, or a material which absorbs substantially no visible light but exhibits supersensitization may be incorporated into the emulsion. Useful sensitizing dyes, combinations of dyes which exhibit supersensitization, and materials which show supersensitization are described in Research Disclosure, Vol. 176, 17643, page 23, Item IV-J (December, 1978), JP-B-49-25500 and JP-B-43-4933, JP-A-59-19032 and JP-A-59-192242, and the like.

The sensitizing dye may be added to the silver halide emulsion by dispersing it directly in the emulsion or may be added to the emulsion after dissolving it in a solvent such as water, methanol, ethanol, propanol, acetone, Methyl Cellosolve, 2,2,3,3-tetrafluoropropanol, 2,2,2-trifluoroethanol, 3-methoxy-1-propanol, 3-methoxy-1-butanol, 1-methoxy-2-propanol and N,N-dimethylformamide; these solvents being used solely or by mixing.

Furthermore, the sensitizing dye may be added using a method disclosed in U.S. Pat. No. 3,469,987 by which the dye is dissolved in a volatile organic solvent, the obtained solution is then dispersed in water or hydrophilic colloid, and the obtained dispersion is added to the emulsion; methods disclosed in JP-B-44-23389, JP-B-44-27555 and JP-B-57-22091 by which the dye is dissolved in an acid, and then the obtained solution is added to the emulsion as it were or in the form of aqueous solution under the presence of acid or base; methods disclosed in U.S. Pat. Nos. 3,822,135 and 4,006,025 by which the dye, under the presence of surfactant, in a form of aqueous solution or colloid dispersion is added to the emulsion; methods disclosed in JP-A-53-102733 and JP-A-58-105141 by which the dye is dispersed directly in hydrophilic colloid and the obtained dispersion is added to the emulsion; or a method disclosed in JP-A-51-74624 by which the dye is dissolved using a compound causing red shift and the obtained solution is added to the emulsion. An ultrasonic wave may also be used in dissolving the dye.

In the preparation of the emulsion, the sensitizing dye may be added in any process steps as far as efficiency of which ever authorized. For example, in the grain formation process of silver halide and/or before desalting, or during the desalting process and/or the time period from desalting up to the initiation of chemical ripening, as disclosed in U.S. Pat. No. 2,735,766, 3,628,960, 4,183,756 and 4,225,666, JP-A-58-184142 and JP-A-60-196749, or immediately before or during the chemical ripening process, or in the time period after chemical ripening up to coating, as disclosed in JP-A-58-113920.

Furthermore, as disclosed in U.S. Pat. No. 4,225,666 and JP-A-58-7629, a single kind of compound per se may be added in parts or the compound in combination with another compound having a different structure may be added in parts, for example, one part is added during grain formation and another part is added during or after the chemical ripening; or one part is added before or during the chemical ripening and another part is added after completion of the chemical ripening. When the compound is added in parts, the compound or combination of the compound added in parts may be altered for each addition process.

An amount of the sensitizing dye used in the present invention may be selected according to the performance such as sensitivity or fog; where it is preferably from $10^{-6}$ to 1 mol per mol of silver halide in the photosensitive layer, and more preferably from $10^{-4}$ to $10^{-1}$ mol.

The silver halide emulsion and/or organic acid silver salt for use in the present invention can successfully be prevented, by addition of an antifoggant, stabilizer or stabilizer precursor, from additional fogging and from lowered sensitivity during the stock storage. Appropriate examples of antifoggants, stabilizers and stabilizer precursors, available individually or in combination, include thiazonium salts described in U.S. Pat. Nos. 2,131,038 and 2,694,716; azaindenes described in U.S. Pat. Nos. 2,886,437 and 2,444,605; mercury salts described in U.S. Pat. No. 2,728,663; urazoles described in U.S. Pat. No. 3,287,135; sulfocatechol described in U.S. Pat. No. 3,235,652; oximes, nitrons and nitroindazoles described in British Patent No. 623,448; polyvalent metal salts described in U.S. Pat. No. 2,839,405; thiuronium salts described in U.S. Pat. No. 3,220,839; palladium, platinum and gold salts described in U.S. Pat. Nos. 2,566,263 and 2,597,915; halogen-substituted organic compounds described in U.S. Pat. Nos. 4,108,665 and 4,442,202; triazines described in U.S. Pat. Nos. 4,128,557, 4,137,079, 4,138,365 and 4,459,350; and phosphorus compounds described in U.S. Pat. No. 4,411,985.

The antifoggant which is preferably used in the present invention is organic halide, and the typical compounds are disclosed in JP-A-50-119624, JP-A-50-120328, JP-A-51-121332, JP-A-54-58022, JP-A-56-70543, JP-A-56-99335, JP-A-59-90842, JP-A-61-129642, JP-A-62-129845, JP-A-6-208191, JP-A-7-5621, JP-A-7-2781, JP-A-8-15809 and U.S. Pat. Nos. 5,340,712, 5,369,000 and 5,464,737.

The antifoggant used in the present invention may be added in any form of solution, powder or solid micrograin dispersion. Dispersion of the solid micrograin is effected using a known pulverizing means (e.g., ball mill, vibrating ball mill, sand mill, colloid mill, jet mill and roller mill). A dispersing agent may be available for dispersing the solid micrograin.

While not being essential for implementing the present invention, it is advantageous in some cases to add a mercury (II) salt as an antifoggant to the emulsion layer. Preferred mercury(II) salts for this purpose are mercury acetate and mercury bromide. The amount of addition of mercury for use in the present invention is preferably from $10^{-9}$ to $10^{-3}$ mol per mol of silver coated, and more preferably from $10^{-8}$ to $10^{-4}$ mol.

The heat-developable photosensitive material of the present invention may contain a benzoic acids for improving the sensitivity and for preventing fog. Any kind of benzoic acid derivatives are available for the present invention, where preferred examples of the structure include those described in U.S. Pat. Nos. 4,784,939 and 4,152,160 and JP-A-9-329863, JP-A-9-329864 and JP-A-9-281637.

Although the benzoic acids for use in the present invention may be added to any portion of the photosensitive material, addition to a layer provided on the same side with the photosensitive layer is preferable, and to an organic acid silver salt-containing layer is more preferable. The benzoic acids may be added at any step during the preparation of the coating liquid. In the case of addition to the fatty acid silver salt-containing layer, the benzoic acids may be added at any step within a period from the preparation of the organic silver salt to the preparation of the coating liquid, where addition in a period following the preparation of the fatty acid silver salt and immediately before the coating is preferable.

The benzoic acids may be added in any form of solution, powder or solid micrograin dispersion. It is also allowable to add the benzoic acids in a form of mixed solution containing other additives such as a sensitizing dye, reducing agent and color toner. An amount of addition of the benzoic acids can arbitrarily set, where a preferable range being from $1 \times 10^{-6}$ to 2 mol per mol of silver, and more preferably from $1 \times 10^{-3}$ to 0.5 mol.

The heat-developable photosensitive material of the present invention may contain mercapto compound, disulfide compound or thione compound so as to control the development by inhibiting or accelerating thereof, to improve the spectral sensitization efficiency, or to improve the storage stability before and after the development.

While any structure of mercapto compound may be available in the present invention, such that expressed by Ar-SM or Ar-S-S-Ar is preferable, wherein M represents a hydrogen atom or alkali metal atom; and Ar represents an aromatic ring or condensed aromatic ring containing one or more nitrogen, sulfur, oxygen, selenium or tellurium atoms. Preferable heteroaromatic rings include benzimidazole, naphthimidazole, benzothiazole, naphthothiazole, benzoxazole, naphthoxazole, benzoselenazole, benzotellurazole, imidazole, oxazole, pyrazole, triazole, thiadiazole, tetrazole, triazine, pyrimidine, pyridazine, pyrazine, pyridine, purine, quinoline and quinazolinone. The heteroaromatic ring may have a substituent selected from, for example, the group consisting of halogen (e.g., Br, Cl), hydroxyl, amino, carboxyl, alkyl (e.g., alkyl having one or more carbon atoms, preferably from 1 to 4 carbon atoms), and alkoxy (e.g., alkoxy having one or more carbon atoms, preferably from 1 to 4 carbon atoms). Examples of the mercapto- substituted heteroaromatic compound include 2-mercaptobenzimidazole; 2-mercaptobenzoxazole; 2-mercaptobenzothiazole; 2-mercapto-5-methylbenzimidazole; 6-ethoxy-2-mercaptobenzothiazole; 2,2'-dithiobis(benzothiazole); 3-mercapto-1,2,4-triazole; 4,5-diphenyl2-imidazolethiol; 2-mercaptoimidazole; 1-ethyl-2-mercaptobenzimidazole; 2-mercaptoquinoline; 8-mercaptopurine; 2-mercapto4 (3H)-quinazolinone; 7-trifluoromethyl-4-quinolinethiol; 2,3,5,6-tetrachloro-4-pyridinethiol; 4-amino-6-hydroxy-2-mercaptopyrimidine monohydrate; 2-amino-5-mercapto-1,3,4-thiadiazole; 3-amino-5-mercapto-1,2,4-triazole; 4-hydroxy-2-mercaptopyrimidine; 2-mercaptopyrimidine, 4,6-diamino-2-mercaptopyrimidine; 2-mercapto-4-methylpyrimidine hydrochloride;3-mercapto-5-phenyl-1,2,4-triazole; and 2-mercapto-4-phenyloxazole; while not particularly being limited thereto.

An amount of the addition, into the emulsion layer, of the mercapto compounds is preferably from 0.001 to 1.0 mol per mol of silver, more preferably from 0.01 to 0.3 mol.

The image-forming layer in the present invention may contain a plasticizer or lubricant, and examples thereof include polyhydric alcohols (for example, glycerin and diol described in U.S. Pat. No. 2,960,404); fatty acid or ester described in U.S. Pat. Nos. 2,588,765 and 3,121,060; and silicone resin described in British Patent No. 955,061.

An ultrahigh contrast agent for producing an image with a ultrahigh contrast may be used in the present invention. Examples of the ultrahigh contrast agent include hydrazine derivatives disclosed in U.S. Pat. Nos. 5,464,738, 5,496,695, 6,512,411, and 5,536,622, JP-A-10-10672, JP-A-10-62898, JP-A-10-31282, JP-A-9-319048, JP-A-9-304870 and JP-A-9-304872; compound having a quaternary nitrogen atom disclosed in JP-A-9-274274; and acrylonitrile compounds disclosed in U.S. Pat. No. 5,545,515. Specific examples of such compounds are exemplified as Compounds 1 to 10 of the above described U.S. Pat. No. 5,464,738; Compounds H-1 to H-28 described in U.S. Pat. No. 5,496,695; Compounds I-1 to I-86 of JP-A-10-10672; Compounds H-1 to H-62 of JP-A-10-62998; Compounds 1-1 to 1-21 of JP-A-10-31282; Compounds 1 to 50 of JP-A-9-304872; Compounds 1 to 40 of JP-A-9-304870; Compounds P-1 to P-26 and Compounds T-1 to T-18 of JP-A-9-274274; and Compounds CN-1 to CN-13 of U.S. Pat. No. 5,545,515.

In the present invention, a contrast accelerator may be used in combination with the above-described ultrahigh contrast agent so as to produce an ultrahigh contrast image. Examples thereof include amine compounds described in U.S. Pat. No. 5,545,505, specifically, AM-1 to AM-5; hydroxamic acids described in U.S. Pat. No. 5,545,507, specifically, HA-1 to HA-11; acrylonitriles described in U.S. Pat. No. 5,545,507, specifically, CN-1 to CN-13; hydrazine compounds described in U.S. Pat. No. 5,558,983, specifically, CA-1 to CA-6; and onium salts described in JP-A-9-297368, specifically, A-1 to A-42, B-1 to B-27 and C-1 to C-14.

Synthetic method, addition method and amount of addition of these ultrahigh contrast agents and contrast accelerators are same as those described in the above-cited patent publications.

The image recording material of the present invention may have a surface protective layer for preventing adhesion of the image-forming layer.

While any kind of polymer is available for a binder contained in the surface protective layer, it is preferable that a polymer having carboxylic acid residues is contained in an amount of 100 mg/m$^2$ to 5 g/m$^2$. The polymers having carboxylic acid residues described herein include natural polymers (e.g., gelatin, alginic acid); modified natural polymers (e.g., carboxymethylcellulose, phthalized gelatin); and synthetic polymers (e.g., polymethacrylate, polyacrylate, polyalkylmethacrylate/acrylate copolymer, polystyrene/polymethacrylate copolymer). A content of the carboxylic acid residues in these polymers is preferably $1 \times 10^{-2}$ to 1.4 mol per 100 g of polymer. The carboxylic acid residues can form salts with, for example, alkali metal ion, alkali earth metal ion and organic cation.

Any kind of adhesion preventive material is available for the surface protective layer in the present invention. Examples of the adhesion preventive material include wax; silica particle; styrene-containing elastomeric block copolymer (e.g., styrene-butadiene-styrene, styrene-isoprene-styrene); cellulose acetate; cellulose acetate butylate; cellulose propionate; and mixtures thereof. The surface protective layer may also contain a crosslinking agent for crosslinking, or a surfactant for improving coating property.

The image producing layer and the surface protective layer therefor in the present invention may contain a light absorbing substance and filter dye as described in U.S. Pat. Nos. 3,253,921, 2,274,782, 2,527,583 and 2,956,879. It is also allowable to dye through mordanting as described, for example, in U.S. Pat. No. 3,282,699. The filter dye is preferably used in an amount so as to attain an absorbance of 0.1 to 3.0, and more preferably 0.2 to 1.5.

The image producing layer or the surface protective layer therefor may contain a matting agent, and examples thereof include starch, titanium dioxide, zinc oxide, silica and polymer beads such as those disclosed in U.S. Pat. Nos. 2,992,101 and 2,701,245. While there is no particular limitation on the degree of matting of the emulsion plane so long as stardust failure does not occur, the Bekk smoothness falls preferably within a range from 50 to 10,000 seconds, and more preferably 80 to 10,000 seconds.

Preparation temperature of the coating liquid for the image producing layer used for the present invention is preferably 30 to 65° C., and more preferably 35 to 60° C. It is also preferable to keep the temperature of the coating liquid for the image producing layer at 30 to 65° C. immediately after the addition of the polymer latex. The reducing agent and organic acid silver salt are preferably mixed with each other before the polymer latex is added.

The organic acid silver salt-containing fluid and the coating liquid for the heat image producing layer are preferably a so-called thixotropic fluid. Thixotropy refers to a property such that the viscosity decreases as the shearing velocity increases. While any type of apparatus is available for viscosity measurement, preferable measurement can be conducted at 25° C. using RFS Fluid Spectrometer manufactured by Rheometric Far East Inc. In the present invention, the viscosity of the organic acid silver salt-containing fluid or the coating liquid for the heat image producing layer under a shearing velocity of 0.1 S$^{-1}$ is preferably 400 to 100,000 mPa.s, and more preferably 500 to 20,000 mPa.s. Such viscosity under a shearing velocity of 1000 S$^{-1}$ is preferably 1 to 200 mPa.s, and more preferably 5 to 80 mPa.s.

There are known various system exerting thixotropy and can be found in "Koza-Reoroji (Rheology Course)" edited by Kobunshi Kanko-kai, and "Kobunshi Ratekkusu (Polymer Latex)" collaborated by Muroi and Morino. It is necessary for the fluid wished to exert thixotropy to contain a large amount of solid micrograins. Thixotropy can advantageously be enhanced by including a thickening linear polymer, increasing an aspect ratio of solid particle with an anisotropic shape, or using an alkali thickener or surfactant.

The heat-developable photographic emulsion used in the present invention forms on the support with one or more layers. In the monolayer Composition, the layer must contain organic silver salt, silver halide, reducing agent and binder, and may additionally contain color toner, coating agent and other auxiliary agents at an option. In the double-layer composition, a first emulsion layer (usually adjacent to the substrate) must contain an organic acid silver salt and a silver halide, and a second layer or both layer must contain some other components. Alternative double-layer composition may be allowable in which a single emulsion layer contains all components and a protective topcoat is provided thereon. A multicolor photosensitive heat-developable photographic material may have a structure such that a combination of the above-described two layers is provided for the respective colors, or, as described in U.S. Pat. No. 4,708,928, a structure such that a single layer contains all components. In the case of a multi-dye multi-color photosensitive heat-developable photographic material, the respective emulsion layers are generally kept away from each other by providing a functional or non-functional barrier layer between the respective photosensitive layers as described in U.S. Pat. No. 4,460,681.

The photosensitive layer in the present invention may contain a dye or pigment of various types so as to improve the color tone or prevent the irradiation. Any dye or pigment is allowable for the photosensitive layer, and the typicals are those listed in the Color Index. Specific examples include organic dyes such as pyrazoloazole dye, anthraquinone dye, azo dye, azomethine dye, oxonole dye, carbocyanine dye, styryl dye, triphenylmethane dye, indoaniline dye and indophenol dye; organic pigments such as azo pigment, polycyclic pigments (phthalocyanine pigments, anthraquinone pigments), dying lake pigment and azine pigment; and inorganic pigments. Preferred examples of the dye for use in the present invention include anthraquinone dyes (e.g., Compounds 1 to 9 described in JP-A-5-341441, Compounds 3-6 to 3-18 and 3-23 to 3-38 described in JP-A-5-165147), azomethine dyes (e.g., Compounds 17 to 47 described in JP-A-5-341441), indoaniline dyes (e.g., Compounds 11 to 19 described in JP-A-5-289227, Compound 47 described in JP-A-5-341441, Compounds 2-10 and 2-11 described in JP-A-5-165147) and azo dyes (Compounds 10 to 16 described in JP-A-5-341441). Preferred examples of the pigment include anthraquinon-base indanthrone dye (e.g., C.I. Pigment Blue 60), phthalocyanine dye (e.g., copper phthalocyanine such as C.I. Pigment Blue 15, and metal-free phthalocyanine such as C.I. Pigment Blue 16), dying lake pigment-base triarylcarbonyl pigment, indigo, and inorganic pigment (e.g., ultramarine blue, cobalt blue).

Such dye or pigment may be added in any form of solution, emulsified product or solid micrograin dispersion or may be added in the state mordanted with a polymer mordant. An amount of such compounds used may be determined according to desired absorbance, and, in general, the compounds are preferably used in an amount of from $1 \times 10^{-6}$ to 1 g per 1 $m^2$ of the photosensitive material. It is also recommendable to use dioxane pigments, quinacridon pigments, diketopyrrolopyrrole pigments or the like to adjust the red tone.

In the present invention, an antihalation layer may be provided on the side more distant from the light source than the image recording layer (photosensitive layer) is. The antihalation layer preferably has a maximum absorbance of 0.3 to 2 in a desired wavelength range, preferably has an absorption of 0.5 to 2 at an exposure wavelength, and preferably has an absorption after processing of 0.001 to 0.5 in the visible wavelength region, and more preferably 0.001 to 0.3.

In the case when an antihalation dye is used in the present invention, the dye may be any compound so long as it has a desired absorption in a desired wavelength region, has a sufficiently low absorption in the visible wavelength region after the processing, and ensures an agreeable absorption spectrum pattern of the antihalation layer. While examples thereof include those described in the following patent publications, the present invention is by no means limited thereto: as a single dye, the compounds described in JP-A-59-56458, JP-A-2-216140, JP-A-7-13295, JP-A-7-11432, U.S. Pat. No. 5,380,635, JP-A-2-68539 (from page 13, left lower column, line 1 to page 14, left lower column, line 9) and JP-A-3-24539 (from page 14, left lower column to page 16, right lower column); and as a dye which is faded after the processing, the compounds described in JP-A-52-139136, JP-A-53-132334, JP-A-56-501480, JP-A-57-16060, JP-A-57-68831, JP-A-57-101835, JP-A-59-182436, JP-A-7-36145, JP-A-7-199409, JP-B-48-33692, JP-B-50-16648, JP-B-2-41734 and U.S. Pat. Nos. 4,088,497, 4,283,487, 4,548,896 and 5,187,049.

The heat-developable photosensitive material of the present invention is preferably of a so-called single-sided type comprising a support having on one side thereof at least one photosensitive layer containing silver halide emulsion and on the other side thereof a back layer.

For the case that the heat-developable photosensitive material of the present invention is of single-sided, a matting agent may be used to improve the transport property. The matting agent appears, in general, as organic or inorganic fine particles insoluble to water. Arbitrary matting agents are available, examples of which include organic matting agents disclosed in U.S. Pat. Nos. 1,939,213, 2,701,245, 2,322,037, 3,262,782, 3,539,344 and 3,767,448; and inorganic matting agents disclosed in U.S. Pat. Nos. 1,260,772, 2,192,241, 3,257,206, 3,370,951, 3,523,022 and 3,769,020; all of which being well known in the related art.

More specifically, the organic compounds available as the matting agent include water-dispersible vinyl polymers such as polymethyl acrylate, polymethyl methacrylate, polyacrylonitrile, acrylonitrile-α-methylstyrene copolymer, polystyrene, styrene-divinylbenzene copolymer, polyvinyl acetate, polyethylene carbonate and polytetrafluoroethylene; cellulose derivatives such as methylcellulose, cellulose acetate, and cellulose acetate propionate; starch derivatives such as carboxystarch, carboxynitrophenylstarch, and urea-formaldehyde-starch reaction product; gelatin hardened with a known hardening agent; and hardened gelatin in a form of fine capsulated hollow particle obtained by coacervate hardening. Preferable examples of the inorganic compounds include silicon dioxide, titanium dioxide, magnesium dioxide, aluminum oxide, barium sulfate, calcium carbonate, silver chloride desensitized by a known method, silver bromide similarly processed, glass and diatom earth.

Different kinds of the matting agent may be combined for use as required. There is no particular limitation on the size or morphology of the matting agent, and those having an arbitrary diameter are available. For implementing the present invention, it is preferable to use a matting agent with a diameter of 0.1 to 30 μm.

Both of wide and narrow particle size distributions of the matting agent are allowable. Since the matting agent strongly affects the haze and surface gloss of the photosensitive material, it is preferable to carefully select the particle size, morphology and particle size distribution of a matting agent at the time of preparing the matting agent, or to mix a plurality of matting agents.

In the present invention, a degree of matting of the back layer is preferably expressed as a Bekk smoothness of 250 to 10 seconds, and more preferably 180 to 50 seconds.

In the present invention, the matting agent is preferably added to an outermost layer or a layer functions as the outermost layer of the photosensitive material, or to a layer provided near the outer surface thereof, and in particular to a layer functions as a so-called protective layer.

The binder preferably applied to the back layer in the present invention is transparent or semi-transparent, colorless in general, and can be made of natural polymer, synthetic resin, polymer and copolymer, as well as other film-forming media such as gelatin, gum arabic, poly (vinyl alcohol), hydroxyethylcellulose, cellulose acetate, cellulose acetate butylate, poly(vinylpyrrolidone), casein, starch, poly (acrylic acid), poly(methyl methacrylate), poly(vinyl chloride), poly(methacrylic acid), copoly(styrene-maleic anhydride), copoly(styrene-acrylonitrile), copoly(styrene-butadiene), polyvinyl acetals [such as poly(vinylformal) and poly(vinylbutyral)], polyesters, polyurethanes, phenoxy resin, poly(vinylidene chloride), polyepoxides, polycarbonates, poly(vinyl acetate), cellulose esters and polyamides. The binder may also be formed by coating from water, organic solvent or emulsion.

In the present invention, the back layer preferably has a maximum absorbance in a desired wavelength region of from approx. 0.3 to 2.0, more preferably 0.5 to 2.0, and preferably has an absorbance after processing of 0.001 to 0.5 in the visible wavelength region, and more preferably 0.001 to 0.3. Examples of the antihalation dye used for the back layer are the same with those for the antihalation layer.

A backside resistive heating layer described in U.S. Pat. Nos. 4,460,681 and 4,374,921 may also be used in the heat-developable photosensitive photographic imaging system.

In the present invention, each layer such as the photosensitive layer, protective layer or back layer may contain a film hardening agent. Various method of use of the film hardening agent are described in "The Theory of the Photographic Process 4th Edition" by T. H. James, published by Macmillan Publishing Co., Inc. (1977), pages 77 to 87, and preferably used are polyvalent metal ion described on page 78 of this publication; polyisocyanates described in U.S. Pat.

No. 4,281,060 and JP-A-6-208193; epoxy compounds described, for example, in U.S. Pat. No. 4,791,042; and vinyl sulfone compounds described, for example, in JP-A-62-89048.

The film hardening agent is added in a form of solution, and preferable timing for adding thereof to the coating liquid for the protective layer resides in a period from 180 minutes before to immediately before the coating, and more preferably from 60 minutes before to 10 seconds before. There is no specific limitation on method or conditions for the mixing provided that sufficient effects of the present invention will be ensured. Specific examples of the method include such that using a tank devised so that an average retention time estimated based on the addition flow rate and feed volume to a coater is adjusted to a desired value; and such that using a static mixer described in Chapter 8 of "Ekitai Kongo Gijutsu (Liquid Mixing Technology)" by N. Harnby, M. F. Edwards, and A. W. Nienow, translated by Koji Takahashi, published by Nikkan Kogyo Shinbun-sha (1989).

Surfactants may preferably used in the present invention to improve the coating property and electric charging. Nonionic, anionic, cationic, fluorine-containing, and any other types of surfactants are properly available. More specifically, they are exemplified as fluorine-containing polymer surfactants disclosed, for example, in JP-A-62-170950 and U.S. Pat. No. 5,380,644; fluorine-containing surfactants disclosed, for example, in JP-A-60-244945 and JP-A-63-188135; polysiloxane-base surfactants disclosed, for example, in U.S. Pat. No. 3,885,965; polyalkylene oxide disclosed, for example, in JP-A-6-301140; and anionic surfactants.

Examples of solvent available for the present invention can be found, for example, in "Shinpan Yozai Poketto Bukku (New Solvent Pocket Book)" published by OHM-sha (1994), while not being limited thereto. Solvents used for the present invention preferably have boiling points within a range from 40 to 180° C.

Examples of the solvents available for the present invention include hexane, cyclohexane, toluene, methanol, ethanol, isopropanol, acetone, methyl ethyl ketone, ethyl acetate, 1,1,1-trichloroethane, tetrahydrofuran, triethyamine, thiophene, trifluoroethanol, perfluoropentane, xylene, n-butanol, phenol, methyl isobutyl ketone, cyclohexanone, butyl acetate, diethyl carbonate, chlorobenzene, dibutyl ether, anisole, ethyleneglycol diethyl ether, N,N-dimethylformamide, morpholine, propane sultone, perfluorotributylamine and water.

The heat-developable photographic emulsion used in the present invention may generally be coated on a variety of supports. Typical supports include polyester film, undercoated polyester film, poly (ethylene terephthalate) film, poly (ethylene naphthalate) film, cellulosenitrate film, cellulose ester film, poly(vinyl acetal) film, polycarbonate film and related resinous material, glass, paper and metal. Typically used are flexible materials such as baryta and/or partially acetylated paper support, and in particular paper support coated with α-olefin polymer; α-olefin polymer being such that having a carbon number of 2 to 10, such as polyethylene, polypropylene and ethylene-butene copolymer. Both of transparent and opaque supports are allowable, the former being more preferable.

The heat-developable photosensitive material of the present invention may have, for an antistatic or conduction promoting purpose, a layer containing or comprising soluble salts (e.g., chloride, nitrate): vapor-deDosited metal; ionic polymers disclosed in U.S. Pat. Nos. 2,861,056 and 3,206,312; and insoluble inorganic salts disclosed in U.S. Pat. No. 3,428,451.

A method for obtaining a color image using the heat-developable photosensitive material of the present invention is described in JP-A-7-13295, from line 43 on page 10 in the left column to line 40 on page 11 in the left column. Stabilizing agents for color dye image are described in British Patent No. 1,326,889, U.S. Pat. Nos. 3,432,300, 3,698,909, 3,574,627, 3,573,050, 3,764,337 and 4,042,394.

The heat-developable photosensitive material in the present invention may be formed by a variety of coating processes, which include extrusion coating, slide coating, curtain coating, dip coating, knife coating, flow coating, and extrusion coating using a specific hopper described in U.S. Pat. No. 2,681,294. In particular, preferable are the extrusion coating and slide coating described together in "Liquid Film Coating" by Stephen F. Kistler and Petert M. Schweizer, published by Chapman and Hall (1997), pages 399 to 536, and the slide coating being more preferable. An exemplary shape of a slide coater used for the slide coating is shown in FIG. 11$b$.1 on page 427 in the above publication. It is also allowable to simultaneously coat two or more layers as required according to the methods described in U.S. Pat. No. 2,761,791 and British Patent No. 837,095.

The heat-developable photosensitive material of the present invention may have additional layers such as dye accepting layer for accepting mobile dye image, opaque layer for effectuating reflective printing, protective top coat layer, and primer layer already known in the field of photothermal photographic technology. It is preferable that the heat-developable photosensitive recording material of the present invention is capable of producing image solely by itself. That is, it is preferable-that the functional layer necessary for producing image, such as image accepting layer, is not provided on the separate material.

While the heat-developable photosensitive material of the present invention can be developed by any method, the development is generally practiced by elevating the temperature of the heat-developable image forming material after image-wise exposure. Preferable development temperature is 80 to 250° C., and more preferably 100 to 140° C. Development time is preferably 1 to 180 seconds, and more preferably 10 to 90 seconds.

The photosensitive material of the present invention may be light-exposed by any method but the light source for the exposure is preferably a laser light. The laser light for use in the present invention is preferably one from a gas laser, YAG laser, dye laser, semiconductor laser or the like. The semiconductor laser as combined with a second harmonic generation device may also be used.

The photosensitive material of the present invention is low in haze at the time of exposure, so that it is liable to generate interference fringes. For preventing the generation of interference fringes, known technique such that guiding a laser light obliquely with respect to the recording material as disclosed in JP-A-5-113548, or such that using a multimode laser disclosed in International Patent Publication WO 95/31754 is preferably used.

The recording material of the present invention is preferably exposed so that loci of the laser lights are overlapped so as to make the scanning lines invisible as described in SPIE, Vol. 169, "Laser Printing", pages 116 to 128 (1979), JP-A-4-51043 and WO 95/31754.

EXAMPLES

The present invention will be explained more specifically hereinafter by referring to the following Examples. The components, amounts of use thereof, ratios, operations and the like mentioned in the following Examples may properly be modified without departing from the spirit of the present invention. The scope of the present invention, therefore, is not limited to the specific Examples described below.

Compounds used in the Examples are shown below:

Spectral Sensitization Dye 1

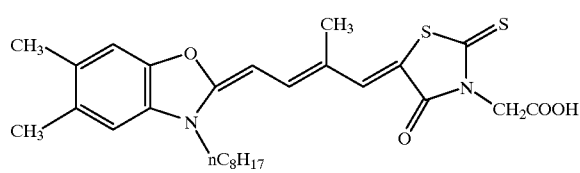

Tellurium Compound

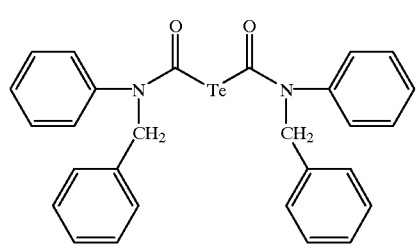

Surfactant "A"

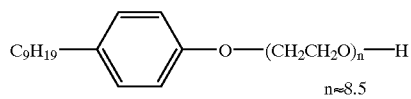

Basic Precursor Compound

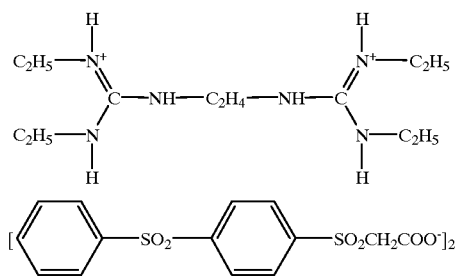

Cyanine Dye Compound

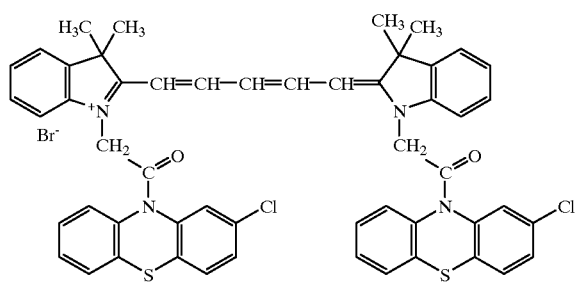

Blue Dye Compound

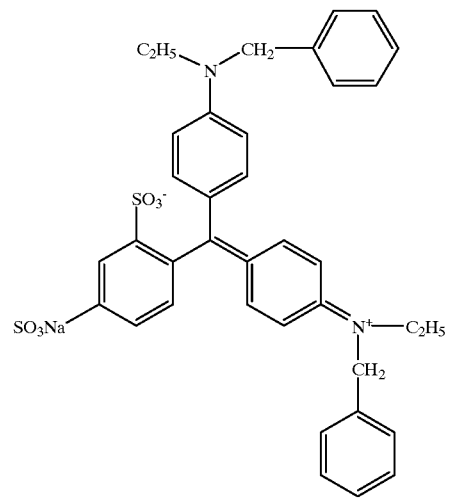

1. Fabrication of PET Support

PET with an intrinsic viscosity (IV) of 0.66 (measured in phenol/tetrachloroethane=6/4 (ratio by weight) at 25° C.) was obtained by the general procedures using terephthalic acid and ethylene glycol. The obtained PET was pelletized, dried at 130° C. for 4 hours, melted at 300° C., extruded from a T-die and rapidly cooled, to obtain a unstretched film so as to have a thickness after heat setting of 175 μm.

The film was then longitudinally stretched 3.3 times at 110° C. using rollers different in the peripheral speed and then transversely stretched 4.5 times at 130° C. using a tenter. Subsequently, the film was heat-set at 240° C. for 20 seconds, and then relaxed by 4% in the transverse direction at the same temperature. Thereafter, a portion chucked by the tenter was slitted off and the film was knurled at the both edges and then taken up. Thus, a rolled support of 175 μm thick was fabricated.

2. Surface Corona Treatment

Using a 6-kVA model of solid state corona treatment apparatus manufactured by Pillar Corporation, the both planes of the support were treated at 20 m/min under the room temperature. Referring to read values of current and voltage, it was confirmed that the support was treated at 0.375 kVA.minute/m². The treatment frequency was 9.6 kHz and the gap clearance between the electrode and dielectric roll was 1.6 mm.

3. Fabrication of Undercoated Support (Preparation of Undercoating Liquid "A")

To 200 ml of a 30 wt % water-base dispersion of polyester copolymer (PESRESIN A-515GB, product of Takamatsu Oil & Fat Co., Ltd.), 1 g of polystyrene micrograin (average particle size of 0.2 μm) and 20 ml of Surfactant "A" (1 wt %) were added, and the total volume was adjusted to 1,000 ml by adding distilled water, thereby to obtain the undercoating liquid "A".

(Preparation of Undercoating Liquid "B")

To 680 ml of distilled water, 200 ml of a 30 wt % water-base dispersion of styrene-butadiene copolymer [syrene/butadiene/itaconic acid=47/50/3 (weight ratio)], 0.1 g of polystyrene micrograin (average grain size of 2.5 μm) were added, and the total volume was adjusted to 1,000 ml by adding distilled water, thereby to obtain the undercoating liquid "B".

(Preparation of Undercoating Liquid "C")

Ten grains of an inert gelatin was dissolved in 500 ml of distilled water, and-thereto 40 g of a 40 wt % water-base dispersion of stannic oxide-antimony oxide complex micrograin described in JP-A-61-20033 was added, and the total volume was adjusted to 1,000 ml by adding distilled water, thereby to obtain the undercoating liquid "C".

(Fabrication of Undercoated Support)

On one plane of the support already treated by the above-described corona discharge treatment, the undercoating liquid "A" was coated using a bar coater with a wet coated amount of 5 ml/m² and was allowed to dry at 180° C. for 5 minutes. The film thickness after the drying was approx. 0.3 µm. On the rear plane (back plane) of the support already treated by the above-described corona discharge treatment, the undercoating liquid "B" was coated using a bar coater with a wet coated amount of 5 ml/m² and then dried at 180° C. for 5 minutes to achieve a dry film thickness of 0.3 µm, and further thereon the undercoating liquid "C" was coated using a bar coater with a wet coated amount of 3 ml/m² and then dried at 180° C. for 5 minutes to achieve a dry film thickness of 0.03 µm.

4. Preparation of Organic Acid Silver Dispersion "A"

(Comparative Example)

While stirring 876 g of behenic acid (Edenor C22-85R, product of Henkel Corporation), 4,230 ml of distilled water and 1,200 ml of tert-butanol at 75° C., added was 492 ml of a 5N aqueous NaOH solution over 5 minutes, then reacted for 60 minutes to obtain sodium behenate solution. Independently, 2,062 ml of aqueous solution containing 404 g of silver nitrate (pH 4.0) was prepared and kept at 10° C. A reaction vessel containing 6,350 ml of distilled water and 300 ml of tert-butanol was kept at 30° C., and an entire volume of the aqueous silver nitrate solution was added at a constant flow rate, and 7 minutes after, addition of an entire volume of the sodium behenate solution was started at a constant flow rate. The addition of the aqueous silver nitrate solution and silver behenate solution took 60 minutes and 62 minutes, respectively. Thus, the last 9 minutes was dedicated to the addition of the sodium behenate solution only. The mixture was allowed to stand for 20 minutes under stirring, and then cooled to 25° C. Solid content was separated by suction filtration, and then washed with water until electric conductivity of the filtrate decreased as low as 30 µS/cm. The obtained solid content was stored in a form of wet cake without drying.

To the obtained wet cake of the organic acid silver, distilled water and polyvinyl alcohol were added according to the composition shown below, and the mixture was then preliminarily dispersed using T. K. Homodisper Model 2M-5 (product of Tokushu Kika Kogyo K.K.) at 5,000 rpm for 15 minutes. The obtained grain was found to have an average grain size of 5.36 µm.

distilled water 424 g organic acid silver (a wet cake with a solid content of 40%) 560 g polyvinyl alcohol (PVA-205, product of Kuraray Co., Ltd.) 22 g The preliminarily dispersed solution was dispersed three times using a dispersion apparatus (Micro Fluidizer M-110S-EH, manufactured by Micro Fluidex International Corporation, equipped with G10Z interaction chamber manufactured by Mizuho Kogyo K.K.) under a pressure of 1,600 kg/cm², to obtain a fatty acid silver salt dispersion "A". Here the temperature control was effected so as to regulate the inlet temperature at 50° C., and the outlet temperature at 30° C. Average particle size and viscosity of the obtained dispersion were 0.56 µm and 18 mPa.s, respectively.

5. Preparation of organic Acid silver Dispersions "B" to "E"

("B" and "C" for Inventive Examepls; "D" and "E" for Comparative Examples)

Sodium behenate and the aqueous silver nitrate solution were added in a similar manner as in the preparation of Dispersion "A" except that the temperature of the mixture was lowered to 15° C. over 20 minutes after the completion of the addition, and that 1,080 ml of a 4 wt % solution of PVA-205 was added. The obtained organic acid silver dispersion was found to have a pH of 6.3. The dispersion is adjusted so as to have the pH values shown in Table 1 using an 1N NaOH solution and an 1N HNO₃ solution, thereby to obtain the persions "B" to "E" before the ultra-filtration.

TABLE 1

| Dispersion | Preparatory method | Dispersing agent Species | Concentration (wt % dispersoid) | Initial pH* | Temp. (° C.) | Poor Solvent | Final Concentration (wt %) |
|---|---|---|---|---|---|---|---|
| A (conventional) | Crystallization + dispersion | PVA | | | | | 22 |
| B | Crystallization + UF | PVA | 10 | 7.6 | 15 | none | 22 |
| C | Crystallization + UF | PVA | 10 | 6.4 | 15 | none | 22 |
| D (comparative) | Crystallization + UF | PVA | 10 | 5.5 | 15 | none | 22 |
| E (comparative) | Crystallization + UF | PVA | 10 | 4.2 | 15 | none | 22 |
| F | Crystallization + UF | PVA | 10 | 6.4 | 5 | none | 22 |
| G | Crystallization + UF | PVA | 10 | 6.4 | 20 | none | 22 |
| H | Crystallization + UF | PVA | 20 | 6.4 | 15 | MeOH | 22 |
| I | Crystallization + UF | PVA | 20 | 6.4 | 15 | EtOH | 22 |
| J | Crystallization + UF | HEC | 10 | 6.4 | 15 | MeOH | 22 |

*Initial pH refers to a pH obtained before the electric conductivity reaches 1,000 µS/cm. PVA = polyvinyl alcohol, HEC = hydroxyethylcellulose, MeOH = methanol, EtOH = ethanol, UF = ultra-filtration The obtained organic acid silver dispersion was then transferred to the ultra-filtration apparatus shown in FIG. 1 and desalted. A membrane module employed here was of a hollow fiber type ACP-1050 (product of Asahi Chemical Industry Co., Ltd.), which was operated at a feeding flow rate of 18 L/minute and a pressure difference between the pre-module stage and post-module stage of 1.0 kg/cm². Concentration of the organic acid silver at that time was found to be approx. 5.5 wt %, which was successively concentrated to a grain concentration of 17 wt % prior to the volume-constant filtration base on continuous replenishment of pure water.

The pH monitoring was continued also during the desalting operation to keep a preset value. The pH adjustment was stopped when the electric conductivity dropped below 1,000 $\mu$S/cm, and the replenishment of pure water was stopped below 100 $\mu$S/cm, which was followed by concentration to 22 wt %. Concentration of the solid content was measured using a digital density meter Model DA-300 (product of Kyoto Denshi K.K.) and was finally determined based on the bone dry weight.

6. Preparation of Organic Acid Silver Dispersions "F" and "G"

(Inventive Examples)

These were prepared in a similar manner as in the preparation of Dispersions "B" to "E", where pH 6.4 was applied for both cases, and the temperature during a period after the addition of PVA-205 and to the completion of the desalting operation was kept at 5° C. (for Dispersion "F") and 20° C. (for Dispersion "G"), respectively.

7. Preparation of Organic Acid Silver Dispersions "H" and "N"

(Inventive Examples)

These were prepared in a similar manner as in the preparation of Dispersions "B" to "E", except that PVA-205 was added as an 8 wt % solution in an amount of 1,080 ml to double the concentration of the dispersing agent, and that 22.5 g of methanol (for Dispersion "H") or ethanol (for Dispersion "I") was added when the electric conductivity dropped to 1,000 $\mu$S/cm.

8. Preparation of Organic Acid Silver Dispersion "J"

(Inventive Examples)

This was prepared in a similar manner as in the preparation of Dispersions "B" to "E", except that, in place of PVA, 1,080 ml of a 4 wt % solution of a nonionic hydroxyethyl-cellulose (HEC) SP550 (product of Dicel Chemical Industries, Ltd.) was added, and that 22.5 g of methanol was added when the electric conductivity dropped to 1,000 $\mu$S/cm similarly to the case of Dispersion "H". Physical properties such as average grain size and viscosity of thus obtained dispersions "A" to "J" are listed in Table 2.

9. Preparation of 25 wt % Dispersion of Reducing Agent

Eighty grains of 1,1-bis(2-hydroxy-3,5-dimethylphenyl)-3,5,5-trimethylhexane and 64 g of a 20 wt % aqueous solution of a modified polyvinyl alcohol (Poval MP-203, product of Kuraray Co., Ltd.) were added with 176 g of water, and then mixed to prepare a slurry. The slurry was then transferred to a vessel of a dispersion apparatus (¼ G Sand Grinder Mill, product of Aimex, Ltd.) together with 800 g of zirconia bead with an average diameter of 0.5 mm and dispersed for 5 hours, thereby to obtain the dispersion of the reducing agent. Reducing agent grain contained in thus obtained dispersion was found to have an average grain size of 0.72 $\mu$m.

10. Preparation of 20 wt % Dispersion of Mercapto Compound

Sixty-four grains of 3-mercapto-4-phenyl-5-heptyl-1,2,4-triazole and 32 g of a 20 wt % aqueous solution of a modified polyvinyl alcohol (Poval MP-203, product of Kuraray Co., Ltd.) were added with 224 g of water, and then mixed to prepare a slurry. The slurry was then transferred to a vessel of a dispersion apparatus (¼ G Sand Grinder Mill, product of Aimex, Ltd.) together with 800 g of zirconia bead with an average diameter of 0.5 mm and dispersed for 10 hours, thereby to obtain the dispersion of the mercapto compound. Mercapto compound grain contained in thus obtained dispersion was found to have an average grain size of 0.67 $\mu$m.

11. Preparation of 30 wt % Dispersion of Organic Polyhalogen Compound

Forty-eight grains of tribromomethylphenylsulfone, 48 g of 3-tribromomethylsulfonyl-4-phenyl-5-tridecyl-1,2,4-triazole and 48 g of a 20 wt % aqueous solution of a modified polyvinyl alcohol (Poval MP-203, product of Kuraray Co., Ltd.) were added with 224 g of water, and then mixed to prepare a slurry. The slurry was then transferred to a vessel of a dispersion apparatus (¼ G Sand Grinder Mill, product of Aimex, Ltd.) together with 800 g of zirconia bead with an average diameter of 0. 5 mm and dispersed for 5 hours, thereby to obtain the dispersion of the organic polyhalogen compound. organic polyhalogen compound grain contained in thus obtained dispersion was found to have an average grain size of 0.74 $\mu$m.

12. Preparation of Methanol Solution of Phthalazine Compound

Twenty-six grains of 6-isopropylphthalazine was dissolved in 100 ml of methanol and used.

13. Preparation of 20 wt % Dispersion of Pigment

Sixty-four grains of C.I. Pigment Blue 60 and 6.4 g of DEMOL-N (product of Kao Corporation) were added with 250 g of water, and then mixed to prepare a slurry. The slurry was then fed into a vessel of a dispersion apparatus (¼G Sand Grinder Mill, product of Aimex, Ltd.) together with 800 g of zirconia bead with an average diameter of 0.5 mm, and dispersed for 25 hours to obtain the pigment dispersion. Pigment grain contained in thus obtained dispersion was found to have an average diameter of 0.21 $\mu$m.

14. Preparation of Silver Halide Emulsion 1

To 1421 ml of distilled water, 6.7 ml of an 1 wt % potassium bromide solution was added, and 8.2 ml of an 1N nitric acid and 21.8 g of phthalized gelatin were further added. The obtained mixture was kept stirred in a titanium-coated stainless reaction vessel at a constant liquid temperature of 35° C., and was then added with an entire volume of solution "a1" obtained by dissolving 37.04 g of silver nitrate in distilled water and diluting it up to 159 ml, by the controlled double jet method at a constant flow rate over 1 minute while keeping pAg at 8.1. Solution "b1" obtained by dissolving 32.6 g of potassium bromide in water and diluting it up to 200 ml was also added by the controlled double jet method. After that, 30 ml of a 3.5 wt % aqueous hydrogen peroxide solution was added, and 336 ml of a 3 wt % aqueous solution of benzimidazole was further added. Solution "a1" was further diluted with distilled water to 317.5 ml to obtain solution "a2", and solution "b1" was further added with dipotassium hexachloroiridate so as to attain a final concentration thereof of $1\times10^{-4}$ mol per mol of silver and diluted with distilled water up to 400 ml, which is a doubled volume of "b1", thereby to obtain solution "b2". Again an entire volume of solution "a2", was added to the mixture by the controlled double jet method at a constant flow rate over 10 minutes while keeping pAg at 8.1. Solution "b2" was also added by the controlled double jet method. After that, the mixture was added with 50 ml of a 0.5% methanol solution of 2-mercapto-5-methylbenzimidazole, the pAg of which was raised to 7.5 with silver nitrate, the pH of which was then adjusted to 3.8 with an 1N sulfuric acid, stopped stirring, subjected to precipitation/desalting/washing processes, added with 3.5 g of deionized gelatin, the pH and pAg thereof were adjusted to 6.0 and 8.2, respectively, with an 1N sodium hydroxide, thereby to obtain the silver halide emulsion.

Grain in the resultant silver halide emulsion was found to be a pure silver bromide grain with an average sphere-equivalent diameter of 0.031 $\mu$m and a sphere-equivalent coefficient of variation of 11%. Grain size and so forth were determined based on an average diameter of 1,000 grains under electron microscopic observation. Ratio of [100] plane of such particle was determined as 85% based on the method of Kubelka-Munk.

The above emulsion was then heated to 50° C. under stirring, added with 5 ml of a 0.5 wt % methanol solution of N,N'-dihydroxy-N", N"-diethylmelamine and 5 ml of a 3.5 wt % methanol solution of phenoxyethanol, and one minute after, sodium benzenethiosulfonate was added in an amount of $3\times10^{-5}$ mol per mol of silver. Two minutes after, the solid dispersion of Spectral Sensitization Dye 1 (aqueous gelatin solution) was added thereto in an amount of $5\times10^{-3}$ mol per mol of silver, and further 2 minutes after, Tellurium Compound was added in an amount of $5\times10^{-5}$ mol per mol of silver, which was followed by ripening for 50 minutes. Immediately before completion of the ripening, 2-mercapto-5-methylbenzimidazole was added in an amount of $1\times10^{-3}$ mol per mol of silver, then the temperature of which was lowered to complete the chemical ripening, thereby to obtain the silver halide emulsion 1.

15. Preparation of Silver Halide Emulsion 2

To 700 ml of water, 22 g of phthalized gelatin and 30 mg of potassium bromide were added, and after conditioned at pH5.0 and 35° C., 159 ml of an aqueous solution containing 18.6 g of silver nitrate and 0.9 g of ammonium nitrate, and an aqueous solution containing potassium bromide and potassium iodide at a molar ratio of 92:8 were added by the controlled double jet method over 10 minutes while keeping the pAg at 7.7. Subsequently, 476 ml of an aqueous solution containing 55.4 g of silver nitrate and 2 g of ammonium nitrate, and an aqueous solution containing $1\times10^{-5}$ mol/L of dipotassium hexachloroiridate and 1 mol/L of potassium bromide were added by the controlled double jet method over 30 minutes while keeping the pAg at 7.7. Thereafter, 1 g of 4-hydroxy-6-methyl-1,3,3a,7-tetraza-indene was added to the mixture, and the pH of which was lowered to cause agglomerative precipitation thereby to effect desalting. Then 0.1 g of phenoxyethanol was added, conditioned at pH5.9 and pAg8.2, to obtain silver iodobromide grain (cubic grain having an 8 wt % iodine-containing core, an average iodine content of 2 wt %, an average grain size of 0.05 $\mu$m, a coefficient of variation of the projected area of 8% and an (100) plane ratio of 88%).

Thus obtained silver halide grain was heated to 60° C., added with 85 $\mu$mol/mol Ag of sodium thiosulfonate, $1.1\times10^{-5}$ mol of 2,3,4,5,6-pentafluorophenyldiphenylphosphine selenide, $1.5\times10^{-5}$ mol of Tellurium Compound, $3.5\times10^{-8}$ mol of chloroauric acid and $2.7\times10^{-4}$ mol of thiocyanic acid, ripened for 120 minutes, rapidly cooled to 40° C., added with $1\times10^{-4}$ mol of Spectral Sensitization Dye 1 and $5\times10^{-4}$ mol of 2-mercapto-5-methylbenzimidazole, and rapidly cooled to 30° C., thereby to obtain a silver halide emulsion 2.

16. Preparation of Coating Liquid for Emulsion Layer

[Coating Liquid "A", "B", "C", "D", "E", "F", "G", "H", "I" and "J"]

To 103 g of each of the above-obtained organic acid silver dispersions "A", "B", "C", "D", "E", "F", "G", "H", "I" and "J", 5 g of a 20 wt % aqueous solution of polyvinyl alcohol PVA-205 (product of Kuraray Co., Ltd.) was added, and the mixture was kept at 40° C., which was further added with 23.2 g of the above-obtained 25 wt % dispersion of the reducing agent, 4.8 g of a 5% aqueous dispersion of C.I. Pigment Blue 60, 10.7 g of the 30 wt % dispersion of the organic polyhalogen compound and 3.1 g of the 20 wt % dispersion of the mercapto compound. Thereafter, 106 g of a 40 wt % SBR latex solution purified by ultrafiltration and kept at 40° C. was added thereto and thoroughly stirred, then 6 ml of the methanol solution of the phthalazine compound was added to obtain organic acid silver-containing liquids "A","B", "C", "D", "E", "F", "G", "H", "I" and "J". Five grains of the silver halide emulsion 1 and 5 g of silver halide emulsion 2 were preliminarily mixed thoroughly, and then added to the above organic acid silver-containing liquid using a static mixer immediately before the coating, which was then directly fed to a coating die so as to attain a coated silver amount of 1.4 g/m².

The above SBR latex purified by ultrafiltration was obtained as follows:

A ten-fold diluted aqueous solution of the SBR latex shown below was purified by dilution using an UF-purification module FS03-FC-FUY03A1 (product of Daicel Membrane-Systems Ltd.) until the ion conductivity dropped to 1.5 mS/cm. The resultant latex concentration was found to be 40 wt %.

SBR latex:

St(68)-Bu(29)-AA(3)-(numerals are for polymerization ratio)

average particle size=0.1 $\mu$m at 45% concentration, electric conductivity=4.2 mS/cm, pH8.2

17. Preparation of Coating Liquid for Intermediate Layer on the Emulsion Plane

[Coating Liquid for Intermediate Layer]

A coating liquid for the intermediate layer was prepared by mixing 772 g of a 10 wt % aqueous solution of polyvinyl alcohol PVA-205 (product of Kuraray Co., Ltd.), 226 g of a 27.5 wt % solution of methyl methacrylate/styrene/2-ethylhexylacrylate/hydroxyethyl methacrylate/acrylic acid copolymer latex (copolymerization ratio by weight of 59/9/26/5/1), 2 ml of a 5 wt % aqueous solution of Aerosol OT (American Cyanamide Corporation), 4 g of benzyl alcohol, 1 g of 2,2,4-trimethyl-1,3-pentanediol monoisobutylate and 10 mg of benzoisothiazolinone, which was then fed to a coating die so as to attain a coating amount of 5 ml/m². Viscosity of the coating liquid measured at 40° C. using a B-type viscometer was found to be 21 mPa. s.

18. Preparation of Coating Liquid for First Protective Layer on the Emulsion Plane

[Coating Liquid for First Protective Layer]

Eighty grains of inert gelatin was dissolved in water, and added thereto were 138 ml of a 10 wt % methanol solution of phthalic acid, 28 ml of an 1N sulfuric acid, 5 ml of a 5 wt % aqueous solution of Aerosol OT (American Cyanamide Corporation) and 1 g of phenoxyethanol, and was further added with water to adjust a total weight to 1,000 g, thereby to obtain a coating liquid, which was then fed to a coating die so as to attain a coating amount of 10 ml/m². Viscosity of the coating liquid measured at 40° C. using a B-type viscometer was found to be 17 mPa.s.

19. Preparation of Coating Liquid for Second Protective Layer on the Emusion Plane

[Coating Liquid for Second Protective Layer]

One hundered grains of inert gelatin was dissolved in water, and added thereto were 20 ml of a 5 wt % aqueous solution of potassium N-perfluorooctylsulfonyl-N-propylalanine, 16 ml of a 5 wt % aqueous solution of Aerosol OT (American Cyanamide Corporation), 25 g of polymethyl methacrylate micrograin (average grain size=4.0 $\mu$m), 44 ml of an 1N sulfuric acid, and 10 mg of benzoisothiazolinone, and was further added with water to adjust a total weight to 1,555 g. The mixture was added with 445 ml of an aqueous solution containing 4 wt % chrome alum and 0.67% of phthalic acid using a static mixer immediately before the coating, and was then fed to a coating die so as to attain a coating amount of 10 ml/m². Viscosity of the coating liquid measured at 40° C. using a B-type viscometer was found to be 9 mPa.S.

21. Fabrication of Heat-Developable Photosensitive Materials "A", "B", "C", "D", "E", "F", "G", "H", "I" and "J"

On the back side of the undercoated support, the coating liquid for the antihalation layer and the coating liquid for the back side protective layer were simultaneously coated in a stacked manner, so as to attain a coated amount of solid content of 0.04 g/m² for the former, and a coated amount of gelatin of 1 g/m² for the latter, respectively. The coated films were then dried to obtain a back layer for preventing halation. On the opposite plane of the back plane, an emulsion layer, an intermediate layer, a first protective layer and a second protective layer were formed in this order by the simultaneous stackable coating based on the slide hopper coating method, thereby to obtain samples of the heat-developable photosensitive materials.

The coating was effected at a speed of 100 m/min while keeping a gap between the end of the coating die and the support at 0.18 mm, and keeping a pressure in a reduced pressure chamber lower by 392 Pa than the atmospheric pressure. In a successive chilling zone, the coated liquid was cooled by a flow of air with a dry-bulb temperature of 18° C. and a wet-bulb temperature of 12° C. at an average wind velocity of 7 m/sec for 30 seconds, and then further dried in a helical floating drying zone by blowing wind with a dry-bulb temperature of 30° C. and a wet-bulb temperature of 18° C. at a blow-out wind velocity from the slit of 20 m/sec for 200 seconds.

22. Evaluation of Photographic Properties

The heat-developable photosensitive materials "A", "B", "C", "D", "E", "F", "G", "H", "I" and "J" thus fabricated were exposed with a semiconductor laser sensitometer (maximum output=500 mW) at 647 nm inclined by 8 degrees from the normal, then subjected to a processing (heat development) at 120° C. for 15 seconds, and the obtained image was measured with a densitometer. Results of the measurement were evaluated by a minimum density (Dmin) and sensitivity [an inverse of a ratio of exposure energies giving Dmin and (Dmin plus 1.0)]. It is understood that higher sensitivity and lower Dmin account for better image producing property.

23. Evaluation of Forced Storability

The heat-developable photosensitive materials "A", "B", "C", "D", "E", "F", "G", "H", "I" and "J" were cut into 30.5 cm×25.4 cm pieces, four corners of which were cut off, and were allowed to stand for a day under a condition of 25° C./50%RH. The pieces were then enclosed in two bags made of a moisture-proof material by tens, and the bags were then allowed to stand in an oven at 50° C. and in a refrigerator at 4° C., respectively. Individual photosensitive materials were then exposed and heat-developed in a similar manner as in the evaluation of the photographic property, where a density at a non-exposed area (Dmin) was assumed to represent fog value.

Rate of increase in fog=[(fog in a hot-stored piece−fog in a cold-stored piece)/(maximum density of a hot-stored piece−fog in a cold-stored piece)]×100

The smaller the rate of increase in fog is, the better the time-dependent storability is.

Properties of the organic acid silver dispersions prepared according to the various conditions, and the photosensitive materials fabricated using thereof were listed in Table 2.

24. Evaluation of Haze

The heat-developable photosensitive materials "A", "B", "C", "D", "E", "F", "G", "H", "I" and "J" were evaluated for haze by organoleptic test, where ⊚ for no turbidity, ○ for good, Δ for light turbidity, x for heavy turbidity and xx for opaque.

TABLE 2

| Dispersion and Photosensitive Material Samples | Grain Size | | Viscosity* (mPa · s) | Filtration Pressure Rise** (kg/cm²) | Photographic Property | | Rate of Increase in fog | Evaluation of Haze |
| --- | --- | --- | --- | --- | --- | --- | --- | --- |
| | Average ($\mu$m) | Coefficient of Variation (%) | | | Dmin | Sensitivity | | |
| A (conventional) | 0.56 | 15 | 18 | 0.08 | 100 | 100 | 1.0 | ⊚ |
| B | 0.46 | 14 | 17 | 0.08 | 101 | 105 | 1.0 | ⊚ |
| C | 0.48 | 14 | 17 | 0.08 | 101 | 105 | 1.1 | ⊚ |
| D (comparative) | 0.49 | 22 | 17 | 0.12 | 107 | 102 | 1.3 | Δ |
| E (comparative) | 0.55 | 37 | 17 | 0.34 | 112 | 100 | 1.5 | X |
| F | 0.45 | 15 | 16 | 0.08 | 101 | 105 | 1.0 | ⊚ |
| G | 0.46 | 14 | 16 | 0.08 | 101 | 105 | 1.0 | ⊚ |
| H | 0.45 | 14 | 36 | 0.08 | 101 | 105 | 1.0 | ⊚ |

TABLE 2-continued

| Dispersion and Photosensitive Material Samples | Grain Size | | Viscosity* (mPa · s) | Filtration Pressure Rise** (kg/cm$^2$) | Photographic Property | | Rate of Increase in fog | Evaluation of Haze |
|---|---|---|---|---|---|---|---|---|
| | Average ($\mu$m) | Coefficient of Variation (%) | | | Dmin | Sensitivity | | |
| I | 0.47 | 14 | 38 | 0.08 | 101 | 105 | 1.0 | ⊚ |
| J | 0.56 | 10 | 27 | 0.10 | 102 | 104 | 1.1 | ⊚ |

*Measured when the electric conductivity was within a range from 900 to 1,000 $\mu$S/cm using a B-type viscometer.
**Difference between the initial pressure and the final pressure after filtering 2 kg of the dispersion was measured using Epocel Filter-EC (product of PAUL) of 1.5 cm diameter at 50 ml/minute.

25. Comparison with Conventional Technology

As compared with dispersion "A" according to the conventional method in which the dispersion is desalted by ultra-filtration, made into a wet cake, and then re-dispersed using a high-pressure homogenizer, the dispersion prepared according to the present invention was found to have in general a smaller average grain size since the primary grains produced upon the crystallization are not ruined during the ultra-filtration nor desalting. Other excellent effects such as improved sensitivity were also obtained presumably because the degree of purification was improved and thereby the photographic property was upgraded due to improved uniformity in the desalting operation. This successfully reduces a coating amount of the organic acid silver salt, which allows a silver-saving formulation and designing.

<<Effects of Initial pH>>

As for dispersions "B" to "E", pH in the initial stage of the ultra-filtration was altered. As compared with dispersions "B" and "C" according to the present invention prepared by adjusting pH at 6 or above before the electric conductivity reached 1,000 $\mu$S/cm, dispersions "D" and "E" prepared by regulating pH below 6 were found to increase in the average grain size and coefficient of variation, and to raise the filtration pressure due to the grain agglomeration. Adverse effects were also found in haze of the photosensitive materials fabricated using thereof. It was also found with regard to dispersions "D" and "E" prepared at a lower pH than that specified in the present invention that Dmin raised and the sensitivity decreased, which resulted in loss of density difference required for obtaining a sharp image. On the contrary, dispersions "B" and "C" according to the present invention were successful in achieving a significant improvement in the sensitivity while a slight increase in Dmin being observed.

<<Effects of Addition of Poor Solvent>>

Effects of the poor solvent added after the electric conductivity of the dispersion fell below 1,000 $\mu$S/cm by the desalting operation on PVA as a dispersing agent were investigated using dispersions "H" and "I". To emphasize the effects of the poor solvent, the PVA concentration relative to the organic acid silver salt was set to 20 wt %, the value being doubled as compared with those for the other series. Dispersions "H" and "I" added with methanol and ethanol, respectively, gave a viscosity of in the order of 30 mPa.s. For the case that such a high concentration of the dispersing agent was employed, the addition of the poor solvent can successfully lower the viscosity of the dispersions and can reduce the flow resistance, which prevented load in the ultra-filtration from being increased, and avoided deterioration in the photographic property.

In conclusion, the present invention can provide an organic acid silver salt dispersion excellent in dispersion stability and coating property, and can also provide a heat-developable photosensitive material having a satisfactory photographic property.

What is claimed is:

1. A method for producing non-photosensitive fatty acid silver salt comprising the steps of reacting a silver ion-containing solution, the solvent of which being a mixture of an organic solvent and water or water, with a solution of an alkali metal salt of a fatty acid, solvent of which being water, organic solvent or a mixture of an organic solvent and water, to obtain a fatty acid silver grain; adding a dispersing agent; and desalting the obtained fatty acid silver dispersion by ultra-filtration;

characterized in that pH of the dispersion is kept at 6 or above during a period from a point of time immediately after the addition of the dispersing agent to a point of time an electric conductivity of the filtrate drops below 2000 $\mu$S/cm but not lower than 500 $\mu$S/cm by the desalting operation.

2. The method for producing non-photosensitive fatty acid silver salt as claimed in claim 1, wherein the pH of the dispersion is kept within a range from 6 to 8 during a period from a point of time immediately after the addition of the dispersing agent to a point of time an electric conductivity of the filtrate drops below 2000 $\mu$S/cm but not lower than 500 $\mu$S/cm by the desalting operation.

3. The method for producing non-photosensitive fatty acid silver salt as claimed in claim 1, wherein temperature of the dispersion of the fatty acid silver grain is kept within a range from 1 to 25° C. during a period from a point of time immediately after the addition of the dispersing agent to a point of time the desalting operation ends.

4. The method for producing non-photosensitive fatty acid silver salt as claimed in claim 3, wherein temperature of the dispersion of the fatty acid silver grain is kept within a range from 5 to 20° C. during a period from a point of time immediately after the addition of the dispersing agent to a point of time the desalting operation ends.

5. The method for producing non-photosensitive fatty acid silver salt as claimed in claim 1, wherein, after the electric conductivity of the filtrate drops below 1000 $\mu$S/cm but not lower than 500 $\mu$S/cm by the desalting operation, the ultra-filtration is continued while adding a poor solvent of the dispersing agent.

6. The method for producing non-photosensitive fatty acid silver salt as claimed in claim 5, wherein the poor solvent of the dispersing agent is methanol or ethanol.

7. The method for producing non-photosensitive fatty acid silver salt as claimed in claim 1, wherein, after the electric conductivity of the filtrate drops below 300 $\mu$S/cm but not lower than 20 $\mu$S/cm by the desalting operation, the dispersion is concentrated to a dispersoid content of 10 to 70 wt %.

8. The method for producing non-photosensitive fatty acid silver salt as claimed in claim 7, wherein the dispersion is concentrated to 20 to 50 wt %.

9. The method for producing non-photosensitive fatty acid silver salt as claimed in claim 1, wherein silver exists in excess of alkali metal by 1 to 20 mol % after the reaction.

10. The method for producing non-photosensitive fatty acid silver salt as claimed in claim 1, wherein the dispersing agent is a nonionic amphiphilic substance.

11. The method for producing non-photosensitive fatty acid silver salt as claimed in claim 1, wherein the dispersing agent is added in an amount of 1 to 30 wt % of the dispersoid.

12. The method for producing non-photosensitive fatty acid silver salt as claimed in claim 11, wherein the dispersing agent is added in an amount of 3 to 20 wt % of the dispersoid.

13. The method for producing non-photosensitive fatty acid silver salt as claimed in claim 1, wherein concentration of the fatty acid silver grain immediately after the reaction is 1 to 10 wt %.

14. The method for producing non-photosensitive fatty acid silver salt as claimed in claim 1, wherein immediately after the desalting operation is completed, the dispersion is concentrated to a fatty acid silver grain content of 15 to 40 wt %.

15. The method for producing non-photosensitive fatty acid silver salt as claimed in claim 14, wherein the desalting operation is performed after the dispersion immediately after the reaction is concentrated to a fatty acid silver grain content of 15 to 25 wt %.

16. The method for producing non-photosensitive fatty acid silver salt as claimed in claim 1, wherein sphere-equivalent diameter of the fatty acid silver grain immediately after the reaction is 0.1 to 0.8 $\mu$m.

17. The method for producing non-photosensitive fatty acid silver salt as claimed in claim 1, wherein long edge/short edge ratio of the fatty acid silver grain immediately after the reaction is 1 to 4.

18. The method for producing non-photosensitive fatty acid silver salt as claimed in claim 1, wherein aspect ratio of the fatty acid silver grain immediately after the reaction is 2 to 30.

19. The method for producing non-photosensitive fatty acid silver salt as claimed in claim 1, wherein thickness of the fatty acid silver grain immediately after the reaction is 0.01 to 0.20 $\mu$m.

20. A heat-developable photosensitive material containing a non-photosensitive fatty acid silver salt, a reducing agent for silver ion, a binder and a photosensitive silver halide grain, characterized in that the non-photosensitive fatty acid silver salt is such that prepared by the method of claim 1.

* * * * *